US009573171B2

(12) United States Patent
Shanahan et al.

(10) Patent No.: US 9,573,171 B2
(45) Date of Patent: Feb. 21, 2017

(54) ELECTROCHEMICAL ACTIVATION OF WATER

(71) Applicant: GenEon Technologies LLC, San Antonio, TX (US)

(72) Inventors: John P. Shanahan, Discovery Bay, CA (US); Remigio Benavides Gonzalez, San Antonio, TX (US)

(73) Assignee: GENEON TECHNOLOGIES LLC, San Antonio, TX (US)

( * ) Notice: Subject to any disclaimer, the term of this patent is extended or adjusted under 35 U.S.C. 154(b) by 0 days.

(21) Appl. No.: 15/192,472

(22) Filed: Jun. 24, 2016

(65) Prior Publication Data

US 2016/0303615 A1  Oct. 20, 2016

Related U.S. Application Data

(63) Continuation of application No. 14/976,324, filed on Dec. 21, 2015, now Pat. No. 9,399,823, which is a
(Continued)

(51) Int. Cl.
| | |
|---|---|
| *C02F 1/46* | (2006.01) |
| *B08B 3/08* | (2006.01) |
| *B08B 3/10* | (2006.01) |
| *B08B 3/02* | (2006.01) |
| *C25B 15/04* | (2006.01) |

(Continued)

(52) U.S. Cl.
CPC ............ *B08B 3/08* (2013.01); *B08B 3/026* (2013.01); *B08B 3/102* (2013.01); *C02F 1/4618* (2013.01); *C02F 1/4674* (2013.01); *C25B 9/12* (2013.01); *C25B 15/02* (2013.01); *C25B 15/04* (2013.01); *C02F 2001/46123* (2013.01); *C02F 2001/46138* (2013.01); *C02F 2201/009* (2013.01); *C02F 2209/29* (2013.01)

(58) Field of Classification Search
CPC ............ B08B 3/08; B08B 3/026; B08B 3/102; C25B 9/12; C25B 15/02; C25B 15/04; C02F 1/4674; C02F 1/4618; C02F 2209/29; C02F 2001/46123; C02F 2001/46138; C02F 2201/009
See application file for complete search history.

(56) References Cited

U.S. PATENT DOCUMENTS 6,705,332 B2 * 3/2004 Field ...................... A47L 11/03
134/100.1

* cited by examiner

*Primary Examiner* — Arun S Phasge
(74) *Attorney, Agent, or Firm* — GTC Law Group PC & Affiliates

(57) ABSTRACT

A floor scrubbing apparatus includes a reservoir for an aqueous salt solution disposed in the floor scrubbing apparatus. An immersion device comprising a submersible housing with at least two iridium-coated electrodes spaced apart from each other within the submersible housing is adapted to be immersed into the reservoir. The floor scrubbing apparatus also includes a control module electrically coupled to the electrodes, wherein the control module controls application of electricity to cause a first electrode to be positively charged and a second electrode to be negatively charged. At least one of a distance and an angle or angles between the at least two iridium-coated electrodes is adjustable for the control module to control the application of electricity to the electrodes in a manner to perform electrochemical activation (ECA) of the aqueous salt solution in the reservoir to create an ECA product solution.

21 Claims, 28 Drawing Sheets

Related U.S. Application Data continuation of application No. 14/055,630, filed on Oct. 16, 2013, now Pat. No. 9,309,601.

(60) Provisional application No. 61/714,601, filed on Oct. 16, 2012.

(51) Int. Cl.
*C25B 15/02* (2006.01)
*C25B 9/12* (2006.01)
*C02F 1/461* (2006.01)
*C02F 1/467* (2006.01)

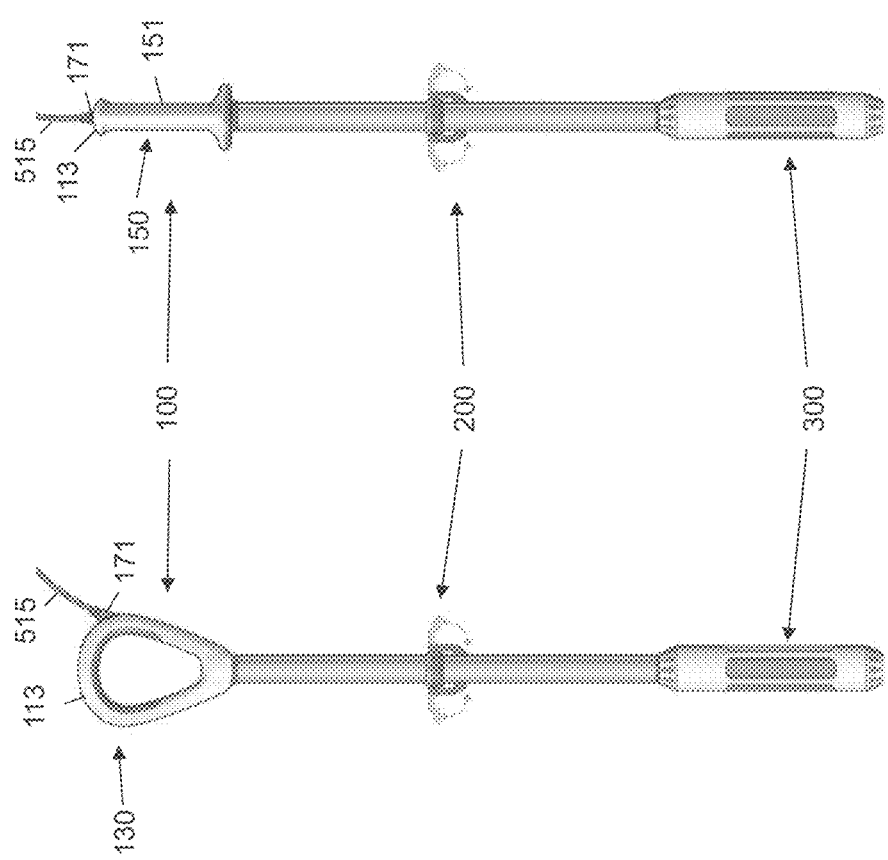

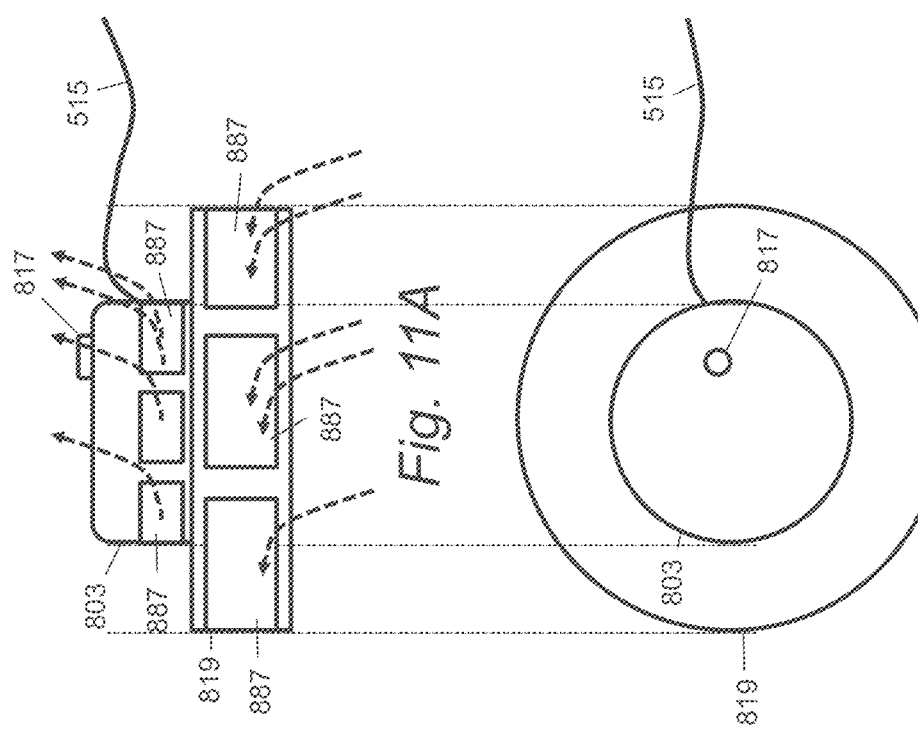

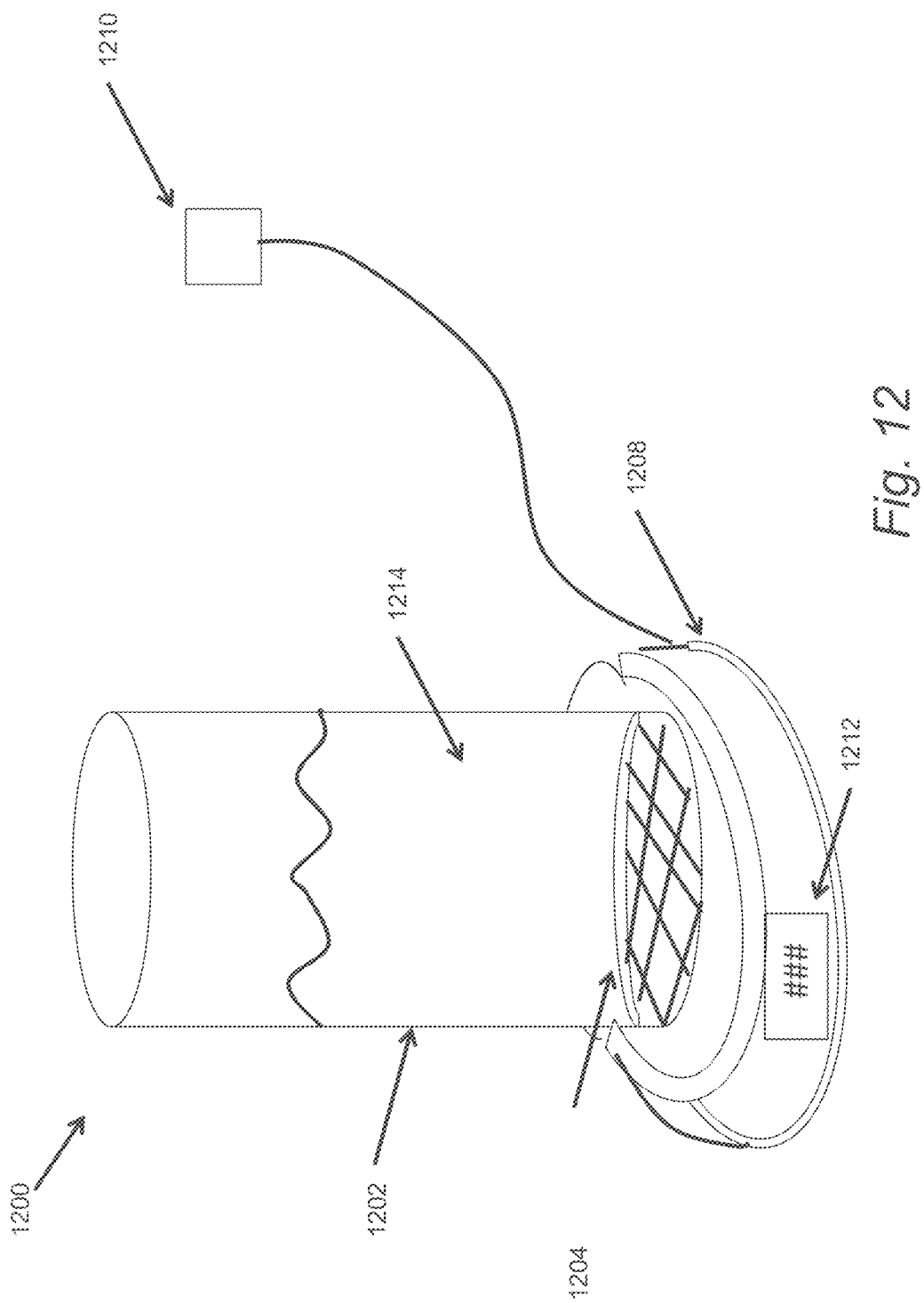

VOLUMETRIC COMPOSITION OF SHALE GAS FRACTURE FLUID

| Parameters | Portable Receptacle Design (TRiO™) | Enlarged Receptacle Design (TRiO-Maxx™) | Medical Receptacle Design (TRiO-Rx™) | Continuous Flow Design (InstaFlow™) | Immersion Wand Design (Immerse-a-Clean™) |
|---|---|---|---|---|---|
| Size of Container / Production | 40 ounces | 64 ounces | 64 ounces | Continuous Flow up to 2.5 Gallons per Minute | Variable/Bulk |
| Technology | ECA-- Blended Stream | ECA-- Blended Stream | ECA-- Blended Stream | ECA-- Blended Stream | ECA-- Blended Stream |
| Catalyst for Cleaner, Sanitizer/ Disinfectant | $K_2CO_3$/NaCl | $K_2CO_3$/NaCl | NaCl ONLY | $K_2CO_3$/NaCl | $K_2CO_3$/NaCl |
| Catalyst for Glass, General Purpose and Heavy Duty Cleaner | Potassium Carbonate | Potassium Carbonate | | Potassium Carbonate | Potassium Carbonate |
| Current Flow | Reversible at half way point through cycle | Reversible at half way point through cycle | Reverses current flow every 2.5 minutes in cycle | Reverses current every 2 minutes in operation | Reverses current every 2 minutes, rests after 2 minutes for 30 second time frame |
| Design assist | Narrowing shape of decanter insures proper mixing of HOCl and Sodium hydroxide. Uses magnet identification system to ensure proper mating with charging base | Wide mouth design provides up to 2 liters, 64 ounces per brewing. Uses magnet identification system to ensure proper mating with charging base | Has paddle system to allow for ultra high FAC production of solution. Has delayed chip activation to provide NaCl to be mixed before ECA process begins. Uses magnet identification system to ensure proper mating with charging base | Utilizes non-membrane technology to provide proper balance of solutions to create the exact amount of Sodium Hydroxide and HOCl to build stable sanitizing solution | Detachable electrodes powered by battery or 110/240 volt allows portability of design. On board air pump engages 5 seconds prior to electrodes to provide agitation for proper mixing of solutions/ or ionized technology. Louvers on end of wand ensure proper ascension of ionization, air vent on bottom ensures proper mixing of supplements in process. Wrist lock handle allows for electrodes to achieve proper orientation in each application. |
| Volt | 110-240 | 110-240 | 110-240 | 110-240 | 110-240/12 volt battery |
| Amp | 4 | 4 | 10 | 17 | 8 to 15 |
| Cycle Time | 5 minutes | 3 to 5 Minutes | 10 Minutes | Continuous | 2/10/Continuous for ionization |
| Electrodes | Iridium | Platinum/Titanium or Iridium | Iridium | Iridium | Iridium |
| Shape of Electrode | Flat Circular 42 cm | Flat Circular 42 cm | Flat Circular 42 cm | Flat/rectangular | Flat/rectangular 9 cm X 11 cm |
| Utility | Portable Table Top Unit | Portable Table Top Unit | Portable Table Top Unit | Stationary Wall Mounted or Table mounted unit. Needs to be connected to a water source and catalyst reservoir(s) | Portable devices that works with 110/240 volts and/or battery powered |
| Products | Produces sanitizing solution with FAC less that 200 ppm. Also produces a glass cleaner, general purpose cleaner and heavy duty cleaner/degreaser | Produces a glass and general purpose cleaner and a heavy duty cleaner/degreaser. It can also produce a sanitizing solution | Produces high FAC disinfectant for health care use with up to 1000 ppm of FAC | Produces a sanitizer, disinfectant, glass cleaner, general purpose cleaner, heavy duty cleaner and degreaser in a continuous flow | Produces a sanitizer, disinfectant, glass cleaner, general purpose cleaner, heavy duty cleaner and degreaser for use in power scrubbers, carpet extractors, tanks, mop buckets, jugs, bottles, and other devices and containers that hold water |

Fig. 14

ELECTROCHEMICAL ACTIVATION OF WATER

CROSS-REFERENCE TO RELATED APPLICATIONS

This application is a continuation of the following U.S. patent applications, each of which is incorporated by reference in its entirety:

U.S. patent application Ser. No. 14/976,324, filed Dec. 21, 2015 (GENE-0001-U01-001). application Ser. No. 14/976,324 is a continuation of U.S. patent application Ser. No. 14/055,630, filed Oct. 16, 2013 (GENE-0001-U01), now U.S. Pat. No. 9,309,601. application Ser. No. 14/055,630 claims the benefit of U.S. Provisional Application No. 61/714,601, filed Oct. 16, 2012 (GENE-0001-P01).

BACKGROUND

Field

The inventive methods and systems described herein generally relate to electrochemical treatment of water to produce cleaning, sanitizing, and antimicrobial solutions.

Description of the Related Art

Many cleaners, sanitizers, disinfectants and antimicrobial products employ harsh chemicals, many of which are toxic. These cause problems when disposed and make their way into the natural water system. Therefore, there have been a number of attempts to make safe and effective cleaners, sanitizers, disinfectants and antimicrobials.

There have been various prior art publications describing electrochemical activation of salt-containing water. It is possible to use these systems for creating solutions useful for cleaning and sanitizing, however, they typically require bulky apparatus and complicated means for separating anolytes and catholytes. There remains a need for cleaning, sanitizing and antimicrobial solutions that are created using harmless compounds in a compact apparatus.

SUMMARY

The present disclosure provides natural, common salts, electrochemically activated in an aqueous solution to result in an ECA product which is safe and non-toxic, with properties of a cleaner, sanitizer, disinfectant, degreaser, antimicrobial and the like. The materials used allow inexpensive production of large amounts of the ECA product at a site where it is being used. This reduces the expenses of purchasing, storing and shipping large amounts of cleaners, sanitizers, degreasers, disinfectants, antimicrobials and the like, especially for large industrial uses.

The systems and methods disclosed herein may include a system, comprising at least two electrodes adapted to be immersed in an aqueous salt solution each disposed at a distance from one another, wherein upon the application of electricity a first electrode is adapted to be positively charged and a second electrode is adapted to be negatively charged and a control module electrically coupled to the electrodes, wherein the control module controls operation of the at least two electrodes and wherein the electrodes are coated with iridium wherein the control module may control the provision of electricity to the electrodes in a manner to perform ECA of the aqueous salt solution to create an ECA product solution. In embodiments, the system may additionally include an ECA product solution selected from a group comprising a sanitizing solution, a disinfecting solution, a cleaning solution, a degreasing solution, and an antimicrobial solution. Additionally, the systems and methods disclosed herein may include a salt that is at least one of sodium chloride and a mixture of sodium chloride and citric acid. The system may include an ECA product solution containing at least HOCl. The system may include a salt which is potassium carbonate. The system may include an ECA product solution containing at least KOH. The system may include a salt which is present in a trace amount. In embodiments, the system may include an ECA product solution containing at least ionized water. The system may include a spray nozzle to distribute the ECA product solution from the system. The system may include a reservoir to collect the ECA product solution. The system may be adapted to provide ECA product solution in a hydraulic fracking application. In embodiments, the system may be adapted to provide ECA product solution in at least one of an airplane, a vehicle, a cruise ship, a humidifier, a vaporizer, a furnace, a floor scrubber, a warewashing facility, a laundry facility, a shower head, a faucet, a food sprayer, and a custodial sprayer. In embodiments, the system may include a control module programmed to reverse the polarity of the electrodes after a pre-determined period of time. Additionally the system may include an impeller for mixing the solution. The system may be powered by at least one of line power, a battery, solar energy and kinetic energy. The system may be deployed such that the distance between the at least two electrodes is adjustable by at least one of a manual mechanism and an automatic mechanism. In embodiments, the system may be deployed such that the distance between the at least two electrodes is adjustable in response to a measurement by a sensor. Additionally, the system may be deployed such the distance between the at least two electrodes is controlled by the control module. The system may include an ECA product solution generated by the operation of the system, wherein the active species is at least one of $OH^-$ and $Cl^-$.

The systems and methods disclosed herein may include a device, comprising a portable receptacle adapted to contain an aqueous solution of a carbonate salt, at least two electrodes spaced apart from each other within the portable receptacle, at least two receptacle contacts being electrical contacts disposed on the container, electrically connected to the electrodes and a base adapted to receive the receptacle and provide electricity to the receptacle contacts, wherein upon the provision of electricity to the receptacle contacts, an electrochemical activation (ECA) of the aqueous solution is caused in the portable receptacle to convert the aqueous solution into an ECA product solution. In embodiments, the device may include a carbonate salt, which may be potassium carbonate ($K_2CO_3$). The device may include a base with a control module that determines the magnitude, timing and polarity of the electricity provided to the electrodes. In embodiments, the electrodes may be made of a highly conductive, non-corrosive metal or made of titanium and have a platinum coating or made of titanium and have an iridium coating. The base and receptacle may include alignment features that cause the receptacle to properly be received by the base. In embodiments, the device may include a receptacle with a magnet and the base includes a sensor for detecting when the magnet is in its vicinity indicating that the receptacle has been received by the base. The device may include a user interface coupled to the control module for indicating at least one of when ECA is progressing and has been completed. In embodiments, the ECA product solution may be selected from the group comprising a sanitizing solution, a disinfecting solution, a cleaning solution, a degreasing solution, and an antimicrobial solution. In embodiments, the ECA product solution may be generated by operation of such a device. Additionally, the active species of the ECA product solution generated may be OH⁻. In embodiments, the salt present with the device may be in a trace amount.

In embodiments, the systems and methods disclosed herein may include a device, comprising a portable receptacle adapted to contain an aqueous solution of a halide salt, at least two electrodes spaced apart from each other within the portable receptacle, at least two receptacle contacts being electrical contacts disposed on the container, electrically connected to the electrodes, and a base adapted to receive the receptacle and provide electricity to the receptacle contacts, wherein upon provision of electricity, an electrochemical activation (ECA) of the aqueous solution in the portable receptacle is caused to convert the aqueous solution into an ECA product solution. In embodiments, the halide salt may be sodium chloride (NaCl) or mixed with citric acid. The base may include a processor that determines the magnitude, timing and polarity of the electricity provided to the electrodes. In embodiments, the ECA product solution may be selected from the group comprising a sanitizing solution, a disinfecting solution, a cleaning solution, a degreasing solution, and an antimicrobial solution. The ECA product solution may be generated by the operation of the device and in certain embodiments, the active species may be Cl⁻. Additionally, the salt present in the device may be present in a trace amount.

The systems and methods disclosed herein may include a device for creating a cleaning solution comprising a portable receptacle adapted to contain water, at least two electrodes spaced apart from each other within the portable receptacle, at least two receptacle contacts being electrical contacts disposed on the container, electrically connected to the electrodes, a base adapted to receive the receptacle and provide electricity to the receptacle contacts, wherein upon provision of electricity, ionization of the water in the portable receptacle is caused to convert the water into a cleaning solution. In embodiments, the systems and methods disclosed herein may include the cleaning solution generated by operation of the device. Additionally, the salt present in the device may be present in a trace amount.

The systems and methods disclosed herein may include an immersion wand device for immersion into a receptacle containing an aqueous carbonate salt solution, comprising, an elongated housing having a handle at a first end and an immersion head at a second end, at least two electrodes spaced apart from each other within the immersion head, a base unit electrically coupled to the electrodes to provide electricity to the electrodes, wherein upon provision of electricity, ECA of the aqueous carbonate salt solution in the receptacle is caused to convert the solution in-situ into an ECA product solution. The elongated housing may be extendable to allow the immersion head to extend to the bottom of various sized receptacles. Additionally, the ECA product solution may be selected from the group comprising a sanitizing solution, a disinfecting solution, a cleaning solution, a degreasing solution, and an antimicrobial solution. ECA product solution may be generated by the operation of the device. Additionally, the active species of the ECA product solution generated by operation of the device may be OH⁻. Furthermore, the salt present in the device may be present in a trace amount.

The systems and methods disclosed herein may include an immersion wand device for immersion into a receptacle containing an aqueous metal halide salt solution, comprising an elongated housing having a handle at a first end and an immersion head at a second end, at least two electrodes spaced apart from each other within the immersion head, a base unit electrically coupled to the electrodes to provide electricity to the electrodes, wherein upon provision of electricity, ECA of the aqueous metal halide salt solution in the receptacle is caused to convert the solution in-situ into an ECA product solution. The elongated housing may extendable to allow the immersion head to extend to the bottom of various sized receptacles. The ECA product solution may be selected from the group comprising a sanitizing solution, a disinfecting solution, a cleaning solution, a degreasing solution, and an antimicrobial solution. An ECA product solution may be generated by the operation of the system or device and/or the disclosed methods. Additionally, the active species of the ECA product solution generated may be Cl⁻. Furthermore, the salt present in the device may be present in a trace amount.

The systems and methods disclosed herein may include a system for creating an ECA product solution from an aqueous metal halide salt solution comprising at least two electrodes adapted to be immersed in the aqueous metal halide salt solution each disposed at a distance from one another, wherein upon application of electricity, a first electrode is adapted to be positively charged and a second electrode is adapted to be negatively charged, and a control module electrically coupled to the electrodes, wherein the control module controls operation of the at least two electrodes. The control module may control the provision of electricity to the electrodes in a manner to perform ECA of the aqueous metal halide salt solution to create an ECA product solution. The system may also include a pump that directs at least one of air, water, or the metal halide salt-containing solution to the at least two electrodes. In embodiments, the metal halide salt may be a metal chloride salt or sodium chloride. The system may operate at variable amperage. In embodiments, the control module causes the system to operate for a specific amount of time to deliver a specific amount of electrical energy. In embodiments, the system may be operated continuously. The salt may be a mixture of sodium chloride and citric acid. The salt may be present in a trace amount. The system may include a control module which causes the system to operate for a specific amount of time to deliver a specific amount of electrical energy to achieve a specific level of Free Available Chlorine. The system may include varying the operation time of the system varies one or more of the products and the concentration of the products of the ECA.

An included pump may be an air pump that pushes air through the solution or a water pump that directs the solution to the at least two electrodes. The pump may be controlled to vary a speed of flow of the solution. In embodiments, the ECA product solution may include at least hypochlorous acid. The system may include electrodes which are iridium-coated. The electrodes may also be disposed at a predetermined spacing for use in ECA. The system may include a sensor that measures at least one of FAC and pH. In embodiments, the control module may be programmed to reverse the polarity of the electrodes after a pre-determined period of time. The system may further include an impeller for mixing the solution. The system may be powered by at least one of line power, a battery, solar energy and kinetic energy. In embodiments, the system may operate at less than or equal to 120 Volts or 240 Volts. The system may operate at 4 Amps, 8 Amps, or at least 10 Amps. In embodiments, the time may be at least one minute, five minutes, or ten minutes. In embodiments, the ECA product solution may be selected from the group comprising a sanitizing solution, a disinfecting solution, a cleaning solution, a degreasing solution, and an antimicrobial solution. The sensor may provide feedback to the control module, wherein the control module modifies operation of the system based on the sensor feedback. The system may further include a user interface in communication with the control module, wherein the user interface is adapted to provide information about the status of at least one of the operation of the system and a condition of the solutions. An ECA product solution may be generated by the operation of the system and/or the disclosed methods, and the active species may be $Cl^-$.

The systems and methods disclosed herein may include a system for creating an ECA product solution from an aqueous carbonate salt solution, comprising at least two electrodes adapted to be immersed in the aqueous carbonate solution each disposed at a distance from one another, wherein upon application of electricity, a first electrode is adapted to be positively charged and a second electrode is adapted to be negatively charged and a control module electrically coupled to the at least two electrodes, wherein the control module controls operation of the at least two electrodes wherein the control module controls the provision of electricity to the electrodes in a manner to perform ECA of the aqueous carbonate solution to create an ECA product solution. The system may also include at a pump that directs at least one of air, water, or the carbonate-containing solution to the at least two electrodes. Additionally, the system may further include an aqueous carbonate salt which is a metal carbonate salt solution of potassium carbonate. In embodiments, the system may operate at variable amperage. The system may include a control module causes the system to operate for a specific amount of time to deliver a specific amount of electrical energy. The system may be operated continuously. The system may include a control module which causes the system to operate for a specific amount of time to deliver a specific amount of electrical energy to achieve a specific level of potassium hydroxide. The system may include varying the operation time of the system varies one or more of the products and the concentration of the products of the ECA. In embodiments, the system may include a pump which is an air pump that pushes air through the solution. The pump may be controlled to vary a speed of flow of the solution. In embodiments, the system may include electrodes that are iridium-coated. In embodiments, the electrodes may be disposed at a predetermined spacing for use in ECA. The system may include a sensor that measures at least one of concentration and pH. In embodiments, the control module may be programmed to reverse the polarity of the electrodes after a pre-determined period of time. In embodiments, the system may include an impeller for mixing the solution. The system may be powered by at least one of line power, a battery, solar energy and kinetic energy. In embodiments, the system may operate at less than or equal to 120 Volts or less than or equal to 240 Volts. The system may operate at 4 Amps, 8 Amps, or at least 10 Amps. In embodiments, the time is at least one minute, at least five minutes, or at least ten minutes. The system may include a sensor which provides feedback to the control module, wherein the control module modifies operation of the system based on the sensor feedback. The system may include a user interface in communication with the control module, wherein the user interface is adapted to provide information about the status of at least one of the operation of the system and a condition of the solutions. The ECA product solution may be selected from the group comprising a sanitizing solution, a disinfecting solution, a cleaning solution, a degreasing solution, and an antimicrobial solution. An ECA product solution may be generated by the operation of the system and/or the disclosed methods. The active species of the ECA product solution may be $OH^-$. The system may include sale which is present in a trace amount.

The systems and methods disclosed herein may include a system comprising a control module that controls the electrical operation of at least two electrodes, the at least two electrodes disposed at a distance from one another in communication with the control module, wherein upon application of electricity, a first electrode is adapted to be positively charged and a second electrode is adapted to be negatively charged, and a pump that is adapted to direct at least one of air or water to the at least two electrodes, wherein the electrodes are adapted to perform electrolysis of water containing trace quantities of salts. In embodiments the electrodes may be iridium-coated. In embodiments, the systems and methods disclosed may comprise a cleaning solution generated by operation of the system. The system may be powered by at least one of line power, a battery, solar energy and kinetic energy. The system may include a sensor that measures parameters of the water. In embodiments, the sensor may provide feedback to the control module, wherein the control module modifies operation of the system based on the sensor feedback. The system may include a user interface of in communication with the control module, wherein the user interface is adapted to provide information about the status of at least one of the operation of the system and a condition of the solutions.

The systems and methods disclosed herein may include a system, comprising a control module that controls the electrical operation of at least two electrodes the at least two electrodes disposed at a distance from one another in communication with the control module, wherein upon application of electricity, a first electrode is adapted to be positively charged and a second electrode is adapted to be negatively charged and a pump that directs at least one of air or water to the at least two electrodes, wherein the electrodes are iridium-coated, and wherein the electrodes are adapted to perform ECA of a salt-containing solution to produce an ECA product solution. In embodiments, the salt may be sodium chloride, a mixture of sodium chloride and citric acid, or potassium carbonate. The salt may also be present in a trace amount. The system may be powered by at least one of line power, a battery, solar energy and kinetic energy. The system may also include a sensor that measures a condition of the salt-containing solution, wherein the sensor provides feedback to the control module and wherein the control module modifies operation of the system based on the sensor feedback. The system may include a user interface in communication with the control module, wherein the user interface is adapted to provide information about the status of at least one of the operation of the system and a condition of the solutions. The distance between the at least two electrodes may be adjustable by at least one of a manual mechanism and an automatic mechanism. In embodiments, the distance between the at least two electrodes may be adjustable in response to a measurement by a sensor. The distance between the at least two electrodes may be controlled by the control module. In embodiments, the ECA product solution may be selected from the group comprising a sanitizing solution, a disinfecting solution, a cleaning solution, a degreasing solution, and an antimicrobial solution. The ECA product solution may be generated by the operation of the system. The active species of the ECA product solution may include at least one of $Cl^-$ and $OH^-$.

The systems and methods disclosed herein may include an immersion device for immersion into a receptacle containing an aqueous metal halide salt solution, comprising a submersible housing, at least two electrodes spaced apart from each other within the submersible housing, a base unit electrically coupled to the electrodes to provide electricity to the electrodes, wherein upon provision of electricity, electrochemical activation (ECA) of the aqueous metal halide salt solution in the receptacle is caused to convert the solution in-situ into an ECA product solution. In embodiments, the aqueous metal halide salt solution is a sodium chloride (NaCl) solution. In embodiments, the distance between the at least two electrodes is adjustable by at least one of a manual mechanism and an automatic mechanism. The distance between the at least two electrodes may be adjustable in response to a measurement by a sensor. The distance between the at least two electrodes may be controlled by a control module in electrical communication with the device. The ECA product solution may be selected from the group comprising a sanitizing solution, a disinfecting solution, a cleaning solution, a degreasing solution, and an antimicrobial solution. The systems and methods disclosed herein may include the ECA product solution generated by operation of the device. The active species of the ECA product solution may be $Cl^-$. In embodiments, the salt may be present in a trace amount.

The systems and methods disclosed herein may include an immersion device for immersion into a receptacle containing an aqueous metal carbonate salt solution, comprising, a submersible housing, at least two electrodes spaced apart from each other within the submersible housing, a base unit electrically coupled to the electrodes to provide electricity to the electrodes, wherein upon provision of electricity, electrochemical activation (ECA) of the aqueous metal carbonate salt solution in the receptacle is caused to convert the solution in-situ into an ECA product solution. The aqueous metal carbonate salt solution is a potassium carbonate ($K_2CO_3$) solution. In embodiments, the distance between the at least two electrodes is adjustable by at least one of a manual mechanism and an automatic mechanism. The distance between the at least two electrodes may be adjustable in response to a measurement by a sensor. In embodiments, the distance between the at least two electrodes may be controlled by a control module in electrical communication with the device. The ECA product solution may be selected from the group comprising a sanitizing solution, a disinfecting solution, a cleaning solution, a degreasing solution, and an antimicrobial solution. The systems and methods disclosed herein, ECA product solution generated by operation of the device. In embodiments, the active species may be $OH^-$. In embodiments, the salt may be present in a trace amount.

A continuous flow system for creating an ECA product solution from a solution of water and a dissolved metal halide salt additive comprising an intake that provides the water to the system, a source of additive that provides metal halide salt to the water to create a solution, a flow conduit that directs the solution through the system, at least two electrodes in the flow conduit adapted to be in contact with the solution, at least one flow control device in the flow conduit that regulates flow through the flow conduit, and a controller coupled to the flow control device adapted to produce a continuous stream of ECA product solution. In embodiments, the system may include at least one flow sensor that determines a flow rate of solution through the system. The system may include at least one chemical sensor that monitors chemical properties of the solution. In embodiments, the controller may be further coupled to at least one flow sensor and at least one chemical sensor to interactively provide power to the electrodes based upon readings from the sensors. In embodiments, the flow control device may be one of an intake valve and an outflow valve. In embodiments, the flow control sensor may be one of an intake sensor and an outflow sensor. In embodiments, the metal halide salt may be metal chloride salt or sodium chloride (NaCl). In embodiments, the system may be adapted to provide the continuous stream in a hydraulic fracking application. Additionally, the system may be adapted to provide the continuous stream in at least one of an airplane, a vehicle, a cruise ship, a humidifier, a vaporizer, a furnace, a floor scrubber, a warewashing facility, a laundry facility, a shower head, a faucet, a food sprayer, and a custodial sprayer. In embodiments, the distance between the at least two electrodes may be adjustable by at least one of a manual mechanism and an automatic mechanism. In embodiments, the distance between the at least two electrodes may be adjustable in response to a measurement by a sensor. Additionally, the distance between the at least two electrodes may be controlled by the controller. In embodiments, the ECA product solution may be selected from the group comprising a sanitizing solution, a disinfecting solution, a cleaning solution, a degreasing solution, and an antimicrobial solution. An ECA product solution may be generated by the operation of the system and/or the disclosed methods. The active species of the ECA product may be $Cl^-$. In embodiments, the salt may be present in a trace amount.

The systems and methods disclosed herein may include a continuous flow system for creating an ECA product solution from a solution of water and a dissolved metal carbonate salt additive comprising an intake that provides the water to the system, a source of additive that provides metal carbonate salt to the water to create a solution, a flow conduit that directs the solution through the system, at least two electrodes in the flow conduit adapted to be in contact with the solution, at least one flow control device in the flow conduit that regulates flow through the flow conduit, and a controller that operates the flow control device adapted to produce a continuous stream of the ECA product solution. The system may include at least one flow sensor that determines a flow rate of solution through the system. The system may also include at least one chemical sensor that monitors chemical properties of the solution. The controller may be further coupled to at least one flow sensor and at least one chemical sensor to interactively provide power to the electrodes based upon readings from the sensors. The flow control device may be one of an intake valve and an outflow valve. The flow control sensor may be one of an intake sensor and an outflow sensor. In embodiments, the metal carbonate salt may be potassium carbonate ($K_2CO_3$). The system may be adapted to provide the continuous stream in a hydraulic fracking application. The system may be adapted to provide the continuous stream in at least one of an airplane, a vehicle, a cruise ship, a humidifier, a vaporizer, a furnace, a floor scrubber, a warewashing facility, a laundry facility, a shower head, a faucet, a food sprayer, and a custodial sprayer. In embodiments, the distance between the at least two electrodes may be adjustable by at least one of a manual mechanism and an automatic mechanism. In embodiments, the distance between the at least two electrodes may be adjustable in response to a measurement by a sensor. In embodiments, the distance between the at least two electrodes may be controlled by the controller. The ECA product solution may be selected from the group comprising a sanitizing solution, a disinfecting solution, a cleaning solution, a degreasing solution, and an antimicrobial solution. An ECA product solution may be generated by the operation of the system and/or the disclosed methods. The ECA product solution may include the active species $OH^-$. In embodiments, the salt may be present in a trace amount.

The systems and methods disclosed herein may include a food treatment system, comprising, at least two electrodes disposed at a distance from one another in communication with a control module, wherein upon application of electricity, a first electrode may be adapted to be positively charged and a second electrode is adapted to be negatively charged the control module electrically coupled to the at least two electrodes, wherein the control module controls operation of the at least two electrodes, and a pump that directs at least one of air, water, or a salt-containing solution to the at least two electrodes, wherein the electrodes are adapted to perform ECA of the salt-containing solution to produce an ECA product solution, wherein the ECA product solution is suitable for treating food. In embodiments, the salt may be sodium chloride or a mixture of sodium chloride and citric acid. The system may include a reservoir to collect the ECA product solution. In embodiments, the salt may be present in a trace amount. The ECA product solution may contain at least HOCl and may contain at least ionized water. In embodiments, the electrodes may be iridium-coated. The system may further include a spray nozzle to distribute the ECA product solution from the system. In embodiments, the salt may be potassium carbonate. The ECA product solution may be selected from the group comprising a sanitizing solution, a disinfecting solution, a cleaning solution, a degreasing solution, and an antimicrobial solution. An ECA product solution may be generated by the operation of the system and/or the disclosed methods. The active species of the ECA product may be $OH^-$ or $Cl^-$.

The systems and methods disclosed herein may include a hand and skin treatment system, comprising at least two electrodes disposed at a distance from one another in communication with the control module, wherein a first electrode is adapted to be positively charged and a second electrode is adapted to be negatively charged upon application of electricity, a control module electrically coupled to the at least two electrodes, wherein the control module controls operation of the at least two electrodes, a pump that directs at least one of air, water, or a salt-containing solution to the at least two electrodes, wherein the electrodes are adapted to perform ECA of the salt-containing solution to produce an ECA product solution, wherein the ECA product solution is suitable for hand and skin treatment. In embodiments, the salt may be sodium chloride or a mixture of sodium chloride and citric acid. In embodiments, the system may include a reservoir to collect the ECA product solution. In embodiments, the salt may be present in a trace amount. In embodiments, the ECA product solution may contain at least HOCl. In embodiments, the ECA product solution may contain at least ionized water. In embodiments, the electrodes may be iridium-coated. In embodiments, the system may include a spray nozzle to distribute the ECA product solution from the system. In embodiments, the salt is potassium carbonate. The ECA product solution may be selected from the group comprising a sanitizing solution, a disinfecting solution, a cleaning solution, a degreasing solution, and an antimicrobial solution. An ECA product solution may be generated by the operation of the system and/or the disclosed methods. The system may include the ECA product solution with active species $OH^-$ or $Cl^-$. In embodiments, the ECA product solution may be an emollient.

The systems and methods disclosed herein may include a surface treatment system, comprising at least two electrodes disposed at a distance from one another in communication with the control module, wherein a first electrode is adapted to be positively charged and a second electrode is adapted to be negatively charged upon application of electricity, a control module electrically coupled to the at least two electrodes, wherein the control module controls operation of the at least two electrodes and a pump that directs at least one of air, water, or a salt-containing solution to the at least two electrodes, wherein the electrodes are adapted to perform ECA of the salt-containing solution to produce an ECA product solution, wherein the ECA product solution is suitable for surface treatment. In embodiments, the salt may be sodium chloride or a mixture of sodium chloride and citric acid. In embodiments, the system may include a reservoir to collect the ECA product solution. In embodiments, the salt may be present in a trace amount. In embodiments, the ECA product solution may contains at least HOCl or at least ionized water. The system may include electrodes which are iridium-coated. Additionally, the system may further include a spray nozzle to distribute the ECA product solution from the system. In embodiments, the system may include salt which is potassium carbonate. The ECA product solution may be selected from the group comprising a sanitizing solution, a disinfecting solution, a cleaning solution, a degreasing solution, and an antimicrobial solution. An ECA product solution may be generated by the operation of the system and/or the disclosed methods. The ECA product solution may include an active species of $OH^-$. The ECA product solution may include an active species $Cl^-$.

The systems and methods disclosed herein may include a method, comprising providing at least two electrodes adapted to be immersed in an aqueous salt solution each disposed at a distance from one another, wherein upon the application of electricity a first electrode is adapted to be positively charged and a second electrode is adapted to be negatively charged and providing a control module electrically coupled to the electrodes, wherein the control module controls operation of the at least two electrodes and wherein the electrodes are coated with iridium wherein the control module may control the provision of electricity to the electrodes in a manner to perform ECA of the aqueous salt solution to create an ECA product solution. In embodiments, the method may generate an ECA product solution selected from a group comprising a sanitizing solution, a disinfecting solution, a cleaning solution, a degreasing solution, and an antimicrobial solution. The salt may be at least one of sodium chloride and a mixture of sodium chloride and citric acid. The ECA product solution may contain at least HOCl. The salt may be at least potassium carbonate. The ECA product solution may contain at least KOH. The salt may be present in a trace amount. The ECA product solution may contain at least ionized water. The method may include using a spray nozzle to distribute the ECA product solution. The method may include using a reservoir to collect the ECA product solution. The method may be adapted to provide ECA product solution in a hydraulic fracking application. In embodiments, the method may be adapted to provide ECA product solution in at least one of an airplane, a vehicle, a cruise ship, a humidifier, a vaporizer, a furnace, a floor scrubber, a warewashing facility, a laundry facility, a shower head, a faucet, a food sprayer, and a custodial sprayer. In embodiments, the method may include using a control module programmed to reverse the polarity of the electrodes after a pre-determined period of time. Additionally the method may include operating an impeller for mixing the solution. The method may include utilizing power from at least one of line power, a battery, solar energy and kinetic energy. The distance between the at least two electrodes may be adjustable by at least one of a manual mechanism and an automatic mechanism. The distance between the at least two electrodes may be adjustable in response to a measurement by a sensor. The distance between the at least two electrodes may be controlled by the control module. An ECA product solution generated by the operation of the method may have active species of at least one of $OH^-$ and $Cl^-$.

The systems and methods disclosed herein may include a method, comprising providing a portable receptacle adapted to contain an aqueous solution of a carbonate salt, providing at least two electrodes spaced apart from each other within the portable receptacle, providing at least two receptacle contacts being electrical contacts disposed on the container, electrically connected to the electrodes; and providing a base adapted to receive the receptacle and provide electricity to the receptacle contacts, wherein upon the provision of electricity to the receptacle contacts, an electrochemical activation (ECA) of the aqueous solution is caused in the portable receptacle to convert the aqueous solution into an ECA product solution.

The systems and methods disclosed herein may include a method, comprising providing a portable receptacle adapted to contain an aqueous solution of a halide salt, providing at least two electrodes spaced apart from each other within the portable receptacle, providing at least two receptacle contacts being electrical contacts disposed on the container, electrically connected to the electrodes, and providing a base adapted to receive the receptacle and provide electricity to the receptacle contacts, wherein upon provision of electricity, an electrochemical activation (ECA) of the aqueous solution in the portable receptacle is caused to convert the aqueous solution into an ECA product solution.

The systems and methods disclosed herein may include a method for creating a cleaning solution comprising, providing a portable receptacle adapted to contain water, providing at least two electrodes spaced apart from each other within the portable receptacle, providing at least two receptacle contacts being electrical contacts disposed on the container, electrically connected to the electrodes, providing a base adapted to receive the receptacle and provide electricity to the receptacle contacts, wherein upon provision of electricity, ionization of the water in the portable receptacle is caused to convert the water into a cleaning solution.

The systems and methods disclosed herein may include a method for providing an immersion wand device for immersion into a receptacle containing an aqueous carbonate salt solution, comprising providing an elongated housing having a handle at a first end and an immersion head at a second end, providing at least two electrodes spaced apart from each other within the immersion head, providing a base unit electrically coupled to the electrodes to provide electricity to the electrodes, wherein upon provision of electricity, ECA of the aqueous carbonate salt solution in the receptacle is caused to convert the solution in-situ into an ECA product solution.

The systems and methods disclosed herein may include a method for providing an immersion wand device for immersion into a receptacle containing an aqueous metal halide salt solution, comprising, providing an elongated housing having a handle at a first end and an immersion head at a second end, providing at least two electrodes spaced apart from each other within the immersion head, providing a base unit electrically coupled to the electrodes to provide electricity to the electrodes, wherein upon provision of electricity, ECA of the aqueous metal halide salt solution in the receptacle is caused to convert the solution in-situ into an ECA product solution.

The systems and methods disclosed herein may include a method for creating an ECA product solution from an aqueous metal halide salt solution comprising, providing at least two electrodes adapted to be immersed in the aqueous metal halide salt solution each disposed at a distance from one another, wherein upon application of electricity, a first electrode is adapted to be positively charged and a second electrode is adapted to be negatively charged, and providing a control module electrically coupled to the electrodes, wherein the control module controls operation of the at least two electrodes wherein the control module controls the provision of electricity to the electrodes in a manner to perform ECA of the aqueous metal halide salt solution to create an ECA product solution.

The systems and methods disclosed herein may include a method for creating an ECA product solution from an aqueous carbonate salt solution, comprising providing at least two electrodes adapted to be immersed in the aqueous carbonate solution each disposed at a distance from one another, wherein upon application of electricity, a first electrode is adapted to be positively charged and a second electrode is adapted to be negatively charged, and providing a control module electrically coupled to the at least two electrodes, wherein the control module controls operation of the at least two electrodes, wherein the control module controls the provision of electricity to the electrodes in a manner to perform ECA of the aqueous carbonate solution to create an ECA product solution.

The systems and methods disclosed herein may include a method, comprising, providing a control module that controls the electrical operation of at least two electrodes, the at least two electrodes disposed at a distance from one another in communication with the control module, wherein upon application of electricity, a first electrode is adapted to be positively charged and a second electrode is adapted to be negatively charged, and providing a pump that is adapted to direct at least one of air or water to the at least two electrodes, wherein the electrodes are adapted to perform electrolysis of water containing trace quantities of salts.

The systems and methods disclosed herein may include a method comprising providing a control module that controls the electrical operation of at least two electrodes, the at least two electrodes disposed at a distance from one another in communication with the control module, wherein upon application of electricity, a first electrode is adapted to be positively charged and a second electrode is adapted to be negatively charged, and providing a pump that directs at least one of air or water to the at least two electrodes, wherein the electrodes are iridium-coated, and wherein the electrodes are adapted to perform ECA of a salt-containing solution to produce an ECA product solution.

The systems and methods disclosed herein may include a method for an immersion device for immersion into a receptacle containing an aqueous metal halide salt solution, comprising, providing a submersible housing, providing at least two electrodes spaced apart from each other within the submersible housing, providing a base unit electrically coupled to the electrodes to provide electricity to the electrodes, wherein upon provision of electricity, electrochemical activation (ECA) of the aqueous metal halide salt solution in the receptacle is caused to convert the solution in-situ into an ECA product solution.

The systems and methods disclosed herein may include a method for an immersion device for immersion into a receptacle containing an aqueous metal carbonate salt solution, comprising, providing a submersible housing, providing at least two electrodes spaced apart from each other within the submersible housing, providing a base unit electrically coupled to the electrodes to provide electricity to the electrodes, wherein upon provision of electricity, electrochemical activation (ECA) of the aqueous metal carbonate salt solution in the receptacle is caused to convert the solution in-situ into an ECA product solution.

The systems and methods disclosed herein may include a continuous flow method for creating an ECA product solution from a solution of water and a dissolved metal halide salt additive comprising, providing an intake that provides the water to the system, providing a source of additive that provides metal halide salt to the water to create a solution, providing a flow conduit that directs the solution through the system, providing at least two electrodes in the flow conduit adapted to be in contact with the solution, providing at least one flow control device in the flow conduit that regulates flow through the flow conduit, and providing a controller coupled to the flow control device adapted to produce a continuous stream of ECA product solution.

The systems and methods disclosed herein may include a continuous flow method for creating an ECA product solution from a solution of water and a dissolved metal carbonate salt additive comprising, providing an intake that provides the water to the system, providing a source of additive that provides metal carbonate salt to the water to create a solution, providing a flow conduit that directs the solution through the system, providing at least two electrodes in the flow conduit adapted to be in contact with the solution, providing at least one flow control device in the flow conduit that regulates flow through the flow conduit, and providing a controller that operates the flow control device adapted to produce a continuous stream of the ECA product solution.

The systems and methods disclosed herein may include a food treatment method, comprising providing at least two electrodes disposed at a distance from one another in communication with a control module, wherein upon application of electricity, a first electrode is adapted to be positively charged and a second electrode is adapted to be negatively charged, providing the control module electrically coupled to the at least two electrodes, wherein the control module controls operation of the at least two electrodes, and providing a pump that directs at least one of air, water, or a salt-containing solution to the at least two electrodes, wherein the electrodes are adapted to perform ECA of the salt-containing solution to produce an ECA product solution, wherein the ECA product solution is suitable for treating food.

The systems and methods disclosed herein may include a hand and skin treatment method, comprising, providing at least two electrodes disposed at a distance from one another in communication with the control module, wherein a first electrode is adapted to be positively charged and a second electrode is adapted to be negatively charged upon application of electricity, providing a control module electrically coupled to the at least two electrodes, wherein the control module controls operation of the at least two electrodes and providing a pump that directs at least one of air, water, or a salt-containing solution to the at least two electrodes, wherein the electrodes are adapted to perform ECA of the salt-containing solution to produce an ECA product solution, wherein the ECA product solution is suitable for hand and skin treatment.

The systems and methods disclosed herein may include a surface treatment method, comprising providing at least two electrodes disposed at a distance from one another in communication with the control module, wherein a first electrode is adapted to be positively charged and a second electrode is adapted to be negatively charged upon application of electricity, providing a control module electrically coupled to the at least two electrodes, wherein the control module controls operation of the at least two electrodes, and providing a pump that directs at least one of air, water, or a salt-containing solution to the at least two electrodes, wherein the electrodes are adapted to perform ECA of the salt-containing solution to produce an ECA product solution, wherein the ECA product solution is suitable for surface treatment.

These and other systems, methods, objects, features, and advantages of the present invention will be apparent to those skilled in the art from the following detailed description of the preferred embodiment and the drawings.

All documents mentioned herein are hereby incorporated in their entirety by reference. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Titles and headings have been added solely for the convenience of the reader and are not intended to limit or reduce the coverage of the descriptions.

BRIEF DESCRIPTION OF THE FIGURES

The invention and the following detailed description of certain embodiments thereof may be understood by reference to the following figures:

FIG. 7 depicts an elevational view of another embodiment, showing a first alternative handle design.

FIG. 8 depicts an elevational view of another embodiment, showing a second alternative handle design.

FIG. 11A depicts an elevational view of another embodiment.

FIG. 11B depicts a plan view of the embodiment shown in FIG. 11A.

FIG. 12 depicts a schematic diagram of an electrode-integrated receptacle apparatus.

FIG. 14 is a table showing various parameters for use of certain embodiments.

DETAILED DESCRIPTION

By applying an electric current to a solution of water and common salts, an electrolysis of the salts in solution occurs, which is known as electrochemical activation or "ECA". Depending on the salt, various products and active species can be generated via ECA. In the prior art, the current was delivered to the solution via an anode and a cathode to produce an electrolyte solution that was separated into both an anolyte and a catholyte. Such separation required various technologies, such as membranes, receptacles, and the like, to separate the anolyte from the catholyte. While delivering electrical current to the solution via an anode and a cathode, the instant application discloses systems and methods of ECA that do not require the separation of the resultant ECA product solution. The instant application discloses a variety of apparati, including embodiments that are handheld, tabletop, wall-mounted, bath, sprayer, floor scrubber, device integrated and many others, for ECA where the salt-containing solution interacts with the electrodes to produce an ECA product solution in a blended stream. Certain of these embodiments are sized to enable portability and/or easy deployment. Certain embodiments are battery-powered to enable portability and various applications where other power sources are not readily available. The ECA product may be environmentally safe cleaners, sanitizers, disinfectants, antimicrobials, degreasers and the like. Further, the instant application discloses various reactants to be used in ECA. One reactant is a sodium chloride (NaCl) and citric acid ($C_6H_8O_7$) mixture wherein ECA produces a product acid comprising a hypochlorous acid (HOCl) solution that exhibits a shelf life of up to 60 days, a pH in the range of about 3-7 and a free available chlorine concentration (FAC) of about 20 ppm to 1000 ppm. Another reactant is potassium carbonate ($K_2CO_3$) wherein ECA produces a product comprising a potassium hydroxide (KOH) solution. In any event, the pH of ECA product solutions produced may range from pH 2 to a high of pH 12. The pH may be lower or higher in certain embodiments. These apparatus, solutions and their various designs and uses are further described herein.

Figure 1:
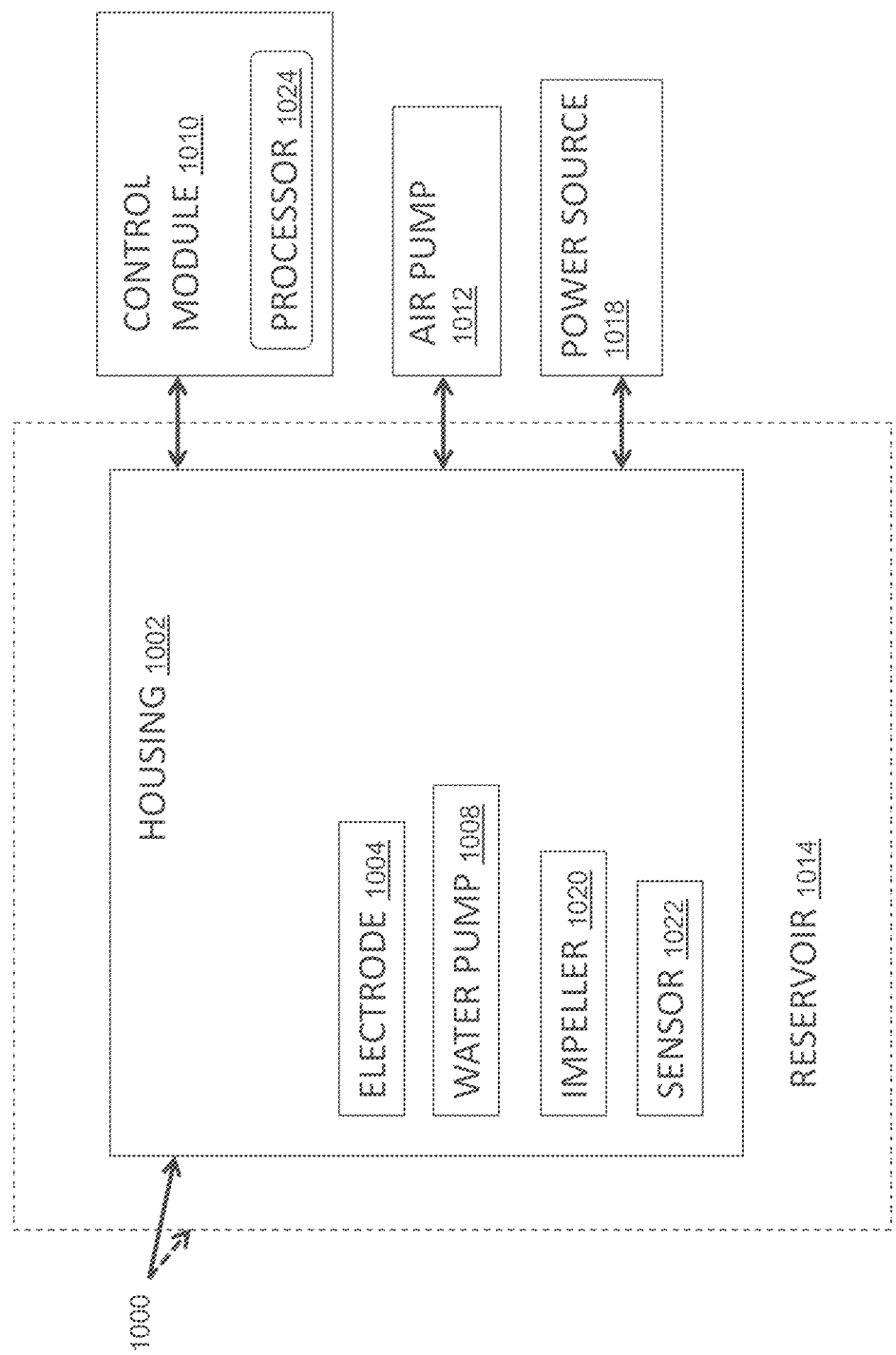
FIG. 1 depicts a block diagram of an ECA system.

Referring now to FIG. 1, a block diagram depicting the various components of an embodiment of an ECA system 1000 as described herein is shown. The ECA system 1000 may include at least two electrodes 1004 but can include more than two in various embodiments, as described herein. A control module 1010 may include a processor 1024 and the necessary memory, programs and logic to control the system. The control module 1010 may provide current to the electrodes 1004 as described herein or may control the current provided by the power source 1018. When the control module 1010 provides a DC current to the electrodes 1004, one electrode 1004 may become positively charged while the other electrode 1004 may be negatively charged, depending on the current flow. In this way, the electrodes 1004 form an anode (the negatively charged electrode 1004) and a cathode (the positively charged electrode 1004). When electrodes 1004 are placed in a liquid, such as water or a salt solution, the electrodes cause an electrolysis reaction in the water or salt solution. The products of the reaction may be allowed to blend as they are formed and as they remain in solution. These reactions are described herein. As shown in FIG. 1 and described in more detail herein, the ECA system 1000 may further include a water pump 1008, impeller 1020, sensor 1022, air pump 1012 and reservoir 1014.

The conductivity of the solution is based upon the amount of dissolved particles in the solution. In a high concentration, the water is very conductive. In a low concentration, the water is less conductive. Low conductivity allows for slower electro-chemical reactions but has less energy dissipated. High conductivity allows for faster electro-chemical reactions, but draws a great deal of power. The amount of power dissipated can cause the electrodes, or system electronics to overheat and to become damaged. Therefore, the spacing between the electrodes is important, as well as the power and duration of the power to provide to the electrodes. A further discussion is provided herein.

The electrodes 1004 may be disposed at a particular distance from one another. The distance between surfaces of the electrodes 1004 may be selected to optimize the operation of the electrodes 1004. For example, the distance may be about 8 mm. In some embodiments, the distance may be less than 8 mm, while in other embodiments the distance may be greater than 8 mm. In any event, the distance may be modified to improve or alter the operation of the electrodes 1004. The electrodes may be mounted on a rack or other attachment system that allows for movement along a continuous path or a path that is limited to obtain set electrode spacing. In other embodiments, the electrodes may be attached at discrete attachment points and the electrodes can be moved between various attachment points to obtain different spacing.

The distance between electrodes may be adjusted manually, automatically, or in response to sensor feedback, such as for example to operate the system with different concentrations of salts, and with different power settings. For example, the electrodes may be automatically adjusted such as when a user inputs a parameter to the system and the optimal electrode distance based on the parameter is different from the current setting. In an embodiment, the distance between the electrodes may be adjusted in response to sensor feedback. For example, as the concentration of HOCl increases as ECA proceeds, the resistance of the solution also increases. A sensor may measure the concentration of FAC, the temperature of the electrodes and/or the resistance of the solution and make an adjustment in the distance of the electrodes in response to the measurement. By making this sensor-based adjustment, the spacing of the electrodes may be kept optimal, such as to keep the temperature in the electrodes from becoming too high. In embodiments, automatic and sensor-based electrode adjustment may be controlled by the control module 1010. In embodiments, while electrodes may generally be disposed in parallel to one another, in other embodiments, electrodes may be disposed at an angle with respect to one another. If the electrodes were angled with respect to each other, most of the current flow would occur where the electrodes are the closest. This may result in uneven reaction rates that may take longer to create a uniform solution. However, as conditions change in the ECA product solution, certain portions of the electrodes may be optimally spaced due to the angling. Indeed, as conditions continue to change in the ECA product solution, other portions of the electrodes may be optimally spaced. By angling the electrodes with respect to one another, the electrodes may on average function well enough, but the range of spacing between the electrodes may be optimal for conditions throughout the reaction.

If it is assumed that the concentration is higher in one location as opposed to other locations, it may be beneficial to adjust the distances between the electrodes accordingly.

Consider, for example, an embodiment where there are three electrodes arranged horizontally parallel to each other each higher that the last. In this embodiment, the top and bottom electrodes would both be either anodes or cathodes with the middle electrode being the opposite polarity. If salt is dropped in the container at the bottom, it has its highest concentration at the bottom with lower concentrations as one moves vertically upward. Therefore, for uniform reactions, one should have the spacing between the lowest and middle electrodes being larger than the spacing between the top and middle electrodes. The differences would be based upon the relative differences in the concentration between each pair of electrodes. In other embodiments, the opposite spacing may be present.

In embodiments, at least two electrodes may be needed by the ECA system 1000. In embodiments, more than two electrodes may be employed by the system. For example, electrodes may operate in pairs, however, the pairs may utilize shared electrodes. For example, an ECA system 1000 may utilize three electrodes. In this configuration, two of the electrodes may be positively charged and one of the electrodes may be negatively charged. The negatively charged electrode may be shared electrode so that two pairs of electrodes are formed in this configuration. When the polarity is reversed in this configuration, only one of the electrodes is positively charged while two of the electrodes are negatively charged and the positively charged electrode is the shared electrode. In embodiments, certain embodiments of the ECA system 1000 may use arrays of a plurality of electrodes, such as might be useful in large scale applications of the ECA system 1000.

Figure 2:
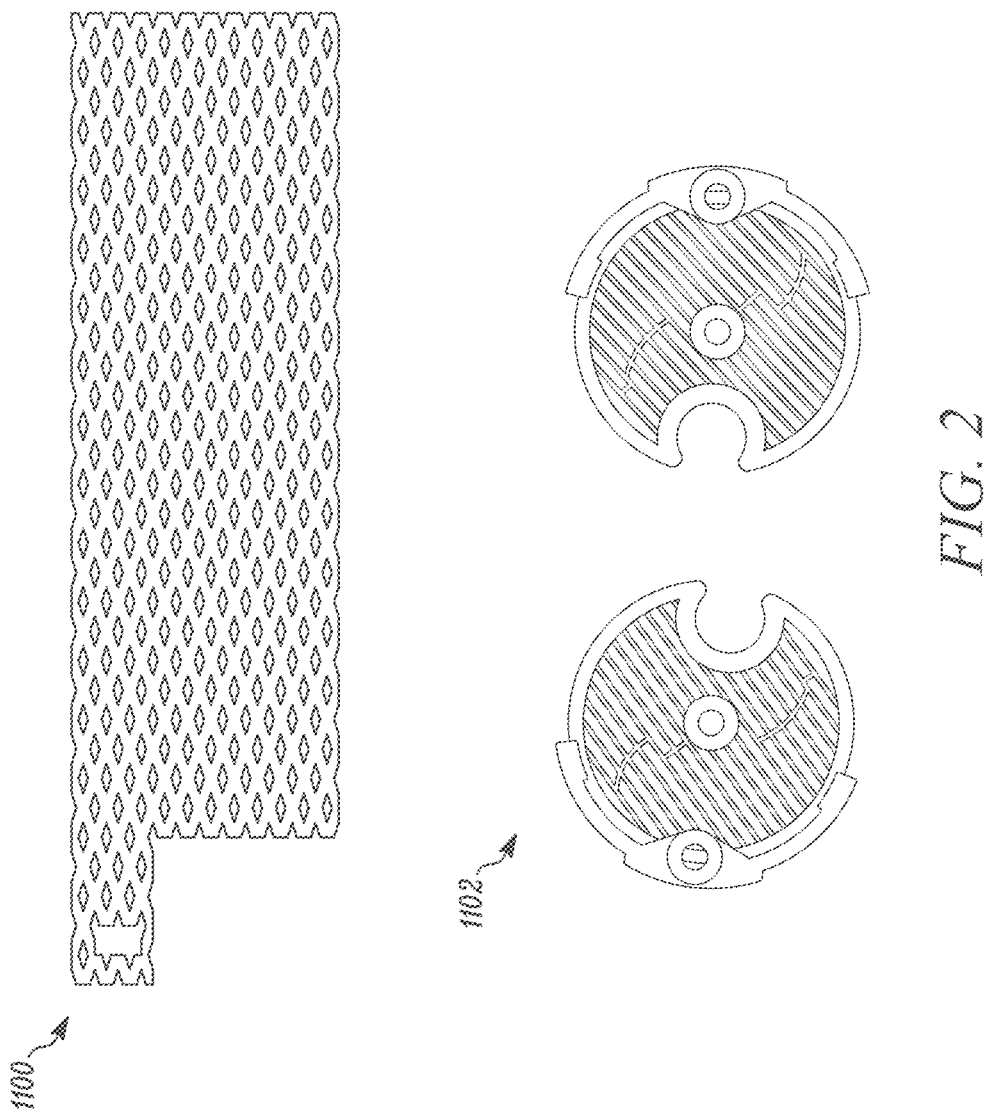
FIG. 2 depicts embodiments of electrodes useful in an ECA system.

In embodiments, the electrodes 1004 may be sized and shaped for particular embodiments and applications of the ECA system 1000. For example, the electrodes 1004 may be in a generally round shape, in a generally rectangular shape, in a generally square shape, or in any other shape or geometry that is conducive to operation as electrodes in the system. For example, FIG. 2 depicts several embodiments of electrodes 1004 in different shapes. Electrode 1100 is shaped in a generally rectangular shape. In certain embodiments, such as in an elongated immersive apparatus embodiment such as that shown in FIGS. 3, 4, 7, 8, and 8A, two or more electrodes 1100 may be disposed adjacent to one another in operation. The generally rectangular shape is conducive to being disposed within the generally elongated apparatus. Electrode 1102 is shaped in a generally circular shape.

The environment in which the electrodes operate is harsh and corrosive to metals. Applying electric current to the electrodes further promotes corrosion. The electrical conductivity of the electrodes decreases as the electrodes become corroded. This causes them to operate in a less efficient manner. The electrodes also tend to warp and lose structural integrity as they corrode. This leads to misaligned electrodes or electrodes that may touch each other and short circuit. Therefore, it is necessary to use materials that both conduct electricity well, and do not corrode.

In an embodiment, the electrodes may include pure forms, oxides or alloys of various metals, such as platinum, titanium, iridium and the like. Other materials are also contemplated for use in electrodes, such as various metals, graphite, and semiconductors.

For example, an embodiment of an electrode 1004 used in the ECA system 1000 is a chip containing an alloy of platinum and titanium coated with pure iridium. In another example, an embodiment of an electrode 1004 used in the ECA system 1000 is a chip containing an alloy of platinum and titanium coated with iridium oxide. In yet another example, an electrode 1004 for use in the ECA system 1000 may be a pure iridium or an iridium oxide electrode.

The iridium coating increases the efficiency with which current is passed through the water or solution. Iridium is a more effective conductor and is substantially resistant to corrosion.

In embodiments, the electrodes 1004 are in communication with the control module 1010. The control module 1010 controls the operation of the electrodes 1004 to perform electrolysis of the components of the water or solution that is in contact with the electrodes 1004. The control module 1010 delivers or controls the delivery of current to the electrodes to maintain either a positive or a negative charge on each electrode 1004. The control module 1010 may include a processor 1024 that has the necessary hardware and software to sense conditions directly or based on input from separate sensors, determine actions and operate the system. In other embodiments, the control module 1010 may include a processor 1024 in communication with external sensors, wherein the processor processes sensor measurements in order to determine conditions, determine actions, and operate the system. The control module 1010 is adapted to control the delivery of current in timed patterns, to modify the voltage, to reverse or modify the polarity, to change the current flowing to the electrodes, to control the speed of flow of water or solution into or through the ECA system, to control the speed of an impeller, and the like.

The control module 1010 can be programmed to control delivery of the current to the electrodes 1004 in a timed fashion. In embodiments, the timing may be selected to generate a particular level of FAC in solution or concentration of another active species, to obtain a particular pH level, to obtain a particular molarity/concentration of products in solution, to obtain completion of a chemical reaction, and the like. In some embodiments, the control module 1010 may deliver current for a period of at least one minute, at least two minutes, at least three minutes, at least four minutes, at least five minutes, at least ten minutes, and the like. In some embodiments, the control module 1010 can be programmed to operate the electrodes 1004 continuously. The control module 1010 may cause the ECA system 1000 to operate for a specific amount of time to deliver a specific amount of electrical energy to the electrodes 1004. The control module 1010 may cause the ECA system 1000 to operate for a specific amount of time to deliver a specific amount of electrical energy to the electrodes 1004 to achieve a specific level of FAC or concentration of another active species. In embodiments, the FAC or concentration of another active species may be determined by a sensor 1022 that feeds back information to the control module 1010 such as to cause operation of the electrodes 1004 to stop when reaching a particular FAC or concentration of another active species or continue if an FAC or concentration of another active species has not been reached. Varying the operation time of the electrodes 1004 of the ECA system 1000 may vary one or more of the products and the concentration of the products in solution after operation of the electrodes 1004.

In an embodiment, the control module 1010 can be programmed to alter the current delivered to the electrodes 1004. Dissolved materials in the water migrate to various electrodes based upon their polarity. For example positively charged calcium ions are drawn toward the anode. Over time, there is a calcium accumulation. In order to minimize this effect, the control module 1010 reverses the polarity of the current provided to the electrodes 1004. In an embodiment, the control module 1010 may be programmed to reverse the polarity of the electrodes 1004 during operation. For example, if the cycle time is 5 minutes, the control module 1010 may be programmed to reverse the polarity of the electrodes at the 2.5 minute mark, or halfway through the cycle. In another embodiment, the control module 1010 may be programmed to reverse the polarity of the electrodes at pre-determined intervals during operation. For example, upon the completion of each two minute period, the control module 1010 may reverse the polarity of the electrodes 1004. In yet another embodiment, the control module 1010 may be programmed to pause operation for a pre-determined period of time during operation. For example, the control module 1010 may be programmed to pause for thirty seconds for every two minutes of operation. In certain embodiments, the pause feature may be combined with the polarity reversal feature. For example, the current delivery may be paused for thirty seconds after two minutes of operation then the polarity may be reversed when operation commences. Reversing the polarity of the electrodes may result in improved electrode operation, such as by limiting calcification of the electrodes.

In an embodiment, the control module 1010 may support operation of the ECA system 1000 at less than or equal to 120 volts or at less than or equal to 240 volts or in other embodiments at higher voltages. In an embodiment, the control module 1010 may support operation of the ECA system 1000 at variable amperage, such as 4 amps, 8 amps, 10 amps, 17 amps, and the like. The amperage may be selected for optimum operation of particular embodiments of the ECA system 1000. For example, while the elongated immersive apparatus may be operated at amperages between 8 and 15, certain versions of the electrode-integrated receptacle apparatus are operated at only 4 amps. Further details of the amperages at use in various embodiments of the ECA system 1000 are further described herein. In some embodiments, the AC current is converted to DC.

In an embodiment of the current invention, the control module 1010 operates to sense various conditions of the system through sensors 1022. For example, a sensor located near the electrodes 1004 may monitor the temperature of the electrodes 1004. During high current flow, these can reach a temperature which may damage the electrodes 1004. The control module 1010 may then reduce the current provided to the electrodes 1004 or stop the current flow until they cool off to an operating temperature.

As indicated above, the control module 1010 may also monitor a sensor 1022 that measures the concentration of the product or active species. It may operate or continue operation of the device until the amount of an active species is reached. It may also increase power provided to the electrodes to increase the measured active species amount if it is below a desired amount. Sensors 1022 external or internal to the ECA system may be adapted to measure pH, concentration (in ppm or FAC), oxygen levels, voltage, resistance, temperature, fluid level, and the like.

The control module may also have an internal logic in the form of a program or other executable commands that would determine if the ECA system may not reach its desired goal of a programmed FAC level. For example, it may have a timeout trigger that monitors the amount of power provided and the change in FAC over a period of time. If it appears that it is not possible to reach the FAC goal within a predetermined amount of time, it will indicate an error reading or other message to the user. This is useful in the case where there is not enough reactant provided to the solution. The control module may be adapted to detect other errors, such as incorrect reactants added to a starting solution, excess reactants added in solution, incorrect reaction conditions, incorrect outputs, early reaction completion as determined by measurement of the ECA product solution or other factors, and the like. For example, if excess reactants are detected, current may be barred from flowing to the electrodes or the amount of current may be increased. Error detection may be aided or enabled by the use of sensors 1022 that feedback to the control module 1010.

The control module 1010 may have an internal logic to determine when too much or too little power is being used by the electrodes. A short circuit will draw a great deal of current. The control module 1010 will sense this draw, such as by an internal or external sensor 1022 that monitors current provided to the electrodes, and shut down the device.

In another situation, there may be no solution between the electrodes. In this case the, the control module 1010 may determine, such as by receiving feedback from a fluid sensor that there is no fluid between the electrodes or by monitoring the activity of the electrodes that no current is being drawn by the electrodes, and shut down the power or not deliver current to the electrodes in the first place.

The control module 1010 may include integrators and clocks to perform a summation/integration of the current provided over time and use this to make decisions. It may also perform an integration/summation of the power dissipated over a period of time, again to make determinations. It may also calculate and provide information on the FAC or concentration of another active species for given periods of time, the periods of time that the unit was operational/non-operational, error reports and other reports.

Embodiments of the ECA system may include a user interface, such as to display visual information or provide audio or electronic information regarding the operation of the system. For example, a display screen may provide the FAC or concentration of another active species, the amount of reactants present or a measure of the elapsed time from starting a particular action or the time to completion of an action or attaining a particular objective. For example, a visual indicator of the user interface may display information regarding the polarity of the electrodes. In the example, when the polarity of the electrodes is in a particular configuration, particular colors or icons may be displayed or animated. When the polarity changes, the visual indicator may become altered to indicate the change in polarity. In a further example, the polarity indicator may be a light or icon that is operated in a first pattern when the current is being applied in a first polarity and a second pattern when the current is being provided in a second polarity. In this embodiment, the lights are in a circular pattern. The lights are lit in a circular pattern in a clockwise direction when it is operating in a first polarity and in a counterclockwise direction when it is operating in a second polarity. In another example, the user interface may provide alerts or information, either visually or in audio, to a user of the ECA system. Such an alert may indicate a pause in the system, a termination of a programmed time of operation, commencement of operation, and the like. Alerts may be tied to sensor operation. For example, a sensor may measure a scarcity of reactants and feedback the information to a control module 1010 in order to generate an alert to a user indicating the scarcity. In another example, a sensor may measure the pH and feedback the information to a control module 1010 in order to generate an alert to a user indicating the pH. In other embodiments, such as large scale operations, messages may be generated and displayed or delivered to a user of the system. All information pertaining to operation of the system and its components may be displayed or otherwise provided by a user interface of the system.

In embodiments, the ECA system 1000 may optionally include a pump. The pump may be an air pump 1012 that directs air through the housing 1002 to support the flow of water or solution through the housing 1002. An air pump 1012 may be useful when the ECA system 1000 is embodied as an elongated immersive apparatus, referred to as the Immerse-A-Clean™ Wand design, as any other immersive apparatus, such as the immersion disk design or as an electrode-integrated portable receptacle design, referred to as the "Trio™", a Medical Receptacle Design referred to as the "Trio Rx™" design and an Enlarged Receptacle Design referred to as "Trio Maxx™". The pump may be a water pump 1008 to direct water or a salt-containing solution to the at least two electrodes 1004. A water pump 1008 may be useful in any apparatus embodying the ECA system 1000. The air pump 1012 or water pump 1008 may be under the control of the control module 1010. For example, the pumps 1008, 1012 may engage for a period of time prior to activation of the electrodes 1004 to provide agitation for proper mixing of the reactants in solution. In another example, the pumps 1008, 1012 are controlled to vary the speed of flow of the water or the solution. In other embodiments, the pumps 1008, 1012 may pump reactants.

In an embodiment, an optional impeller 1020 may be included in the ECA system 1000. Certain embodiments of the ECA system 1000, such as the elongated immersive apparatus, may include an impeller 1020 within the housing 1002 to mix solution contained within the housing 1002. Alternatively, the impeller 1020 may be mounted on an end of, on a surface of, or around the housing 1002 to agitate the solution in which the apparatus is immersed. In other embodiments, such as an electrode-integrated portable receptacle designs, the impeller 1020 may be disposed in a lower portion of the receptacle. The impeller 1020 may be removably connected. In some embodiments, the impeller 1020 may operate using magnetic forces. The impeller 1020 may be under the control of the control module 1010. For example, the control module 1010 may time the operation of the impeller 1020 so that the impeller 1020 operates for a sufficient amount of time to ensure the adequate mixing of the reactants into solution prior to commencing electrode 1004 activation.

In an embodiment, the ECA system 1000 may be powered by various power sources 1018. For example, the ECA system 1000 may operate on an alternating current power supply. The power can be supplied at various voltages between 110 volts and 240 volts or other voltages. All of the embodiments described herein may work with standard household voltage of 120/240 VAC. The 110 volt power may be stepped down to 12 volts (or other voltages) for safety or other reasons, to power devices embodying the system, and/or charge the system battery. The ECA system 1000 may operate on a car charger, an external battery pack, a wall plug, and the like. A power cord of the ECA system 1000 may be adapted to terminate in a way to facilitate receiving power from many different sources. For example, in FIG. 8A, a USB cord 470 connects a control module/air pump 472 of the immersive wand to either a 110 V wall plug 474, a 12V car charger 478, or a battery pack 480. The ECA system 1000 may operate on solar energy. For example, a component of the ECA system 1000 itself, such as the housing 1002 or the control module 1010, may support a solar cell for collecting solar energy. Appropriate electronics for converting the solar energy for use in the ECA system 1000 may be included in the ECA system 1000, such as in the control module 1010. In certain embodiments, the ECA system 1000 may operate on battery power, such as on a 12 volt battery. The battery may be a part of the ECA system or may be part a device into which the ECA system is integrated. The power source may include a 12 volt converter attached to certain equipment. The battery may be rechargeable or disposable. In other embodiments, the ECA system 1000 may be powered by using kinetic energy harnessed by a generator of the ECA system 1000. For example, a hand crank generator may be disposed on the elongated immersive apparatus or on its control module 1010 or otherwise in electrical communication with the apparatus or components thereof. For example, the kinetic energy may result from the cleaning motion of the device, for example, as a result of a user using the device. In another example, the ECA system embodied in or as a floor scrubber may be powered by the kinetic energy generated from moving the floor scrubber. In embodiments, power may be supplied as an alternating current (AC) or in other embodiments as direct current (DC). In other embodiments, the power supplied as AC may first be converted to DC before its use in the ECA system. Embodiments of the ECA system may include quick-connect battery terminals for powered cleaning equipment. Embodiments of the ECA system may include an on-board ground fault circuit interrupter (GFCI) or other GFCI technology. In embodiments, the ECA system, possibly the power source, may include one or more fuses.

In an embodiment, the ECA system 1000 may optionally include one or more sensors 1022. The sensor 1022 may be adapted to determine any of pH, FAC/ppm, $Cl^-$ amounts, $OH^-$ amounts, oxygen amounts, ion amounts, temperature, alkalinity, acidity, particulate level, pathogen level, volume, pressure, fluid presence/moisture, specific reactants, specific active species, voltage, current, resistance and the like. Sensor 1022 feedback to a control module 1010 of the ECA system 1000 may cause a change in control of a parameter of the ECA system 1000. For example, if the sensor 1022 determines that a particular pH has been reached in solution, the control module 1010 may use the sensor 1022 reading as an indication that electrode 1004 activation should terminate.

In the embodiment employing continuous flow, sensors 1022 are included that may monitor the rate of input flow, the reservoir fluid level, the rate of output fluid flow and the like. It may also measure concentrations of various chemical entities entering the system, in its reservoir and exiting the system. The sensors 1022 may determine handoff from one component of the system to another.

A sensor 1022 may be a voltmeter or over-volt meter or multi-meter to indicate how much voltage or current is being applied to or across the electrodes. The voltmeter can tie in to an auto safety shut off. Feedback from the voltmeter may cause a user to vary a setting of the system, such as the amperage.

The ECA system 1000 may include a reservoir 1014 in various embodiments. For example, the reservoir 1014 may be a receptacle exterior to the ECA system 1000 into which the ECA product solution may flow, such as when the ECA system 1000 is embodied in an instant flow apparatus, which is described herein. In another example, the reservoir 1014 may be a receptacle exterior to the ECA system 1000 into which an apparatus embodying the system, such as an immersive apparatus, may be placed. In this example, the reactants may be placed in solution in the reservoir 1014 and at least a portion of the immersive apparatus may be placed into the reservoir 1014 containing the reactant solution. In yet other embodiments, such as when the ECA system 1000 is embodied in an electrode-integrated receptacle apparatus, the reservoir 1014 may be the receptacle itself. The electrodes 1004 are constantly exposed to solution in the reservoir 1014 as they are integrated into the receptacle.

The ECA system 1000 may enable various salt-mediated electrolysis reactions to electrochemically activate water. In embodiments, the salts may be present in trace amounts in a municipal water supply. In other embodiments, the salts may be added to a reactant solution as the reaction proceeds. In any event, solutions produced by the ECA system 1000 may be useful for sanitization, disinfecting, antimicrobial applications, aseptic applications, cleaning, and the like, as further described herein. According to the FDA, "sanitization" means the application of cumulative heat or chemicals on cleaned food-contact surfaces that, when evaluated for efficacy, is sufficient to yield a reduction of 5 logs, which is equal to a 99.999% reduction, of representative disease microorganisms of public health importance. Typically, sanitizing solutions are regulated by law in accordance with 21 CFR 178.1010 to provide not more than 200 ppm of available halogen determined as FAC. US FIFRA Act 7 U.S.C. Section 136g (C)(3) Section 12(a)(1)(A) governs the designation of disinfectants that contain greater than 200 ppm. In certain embodiments herein, the terms sanitizer and disinfectant may have these meanings.

In one example, the starting material for the ECA system 1000 is a mixture of sodium chloride and citric acid. In an embodiment, the citric acid is blended with the sodium chloride in a ratio sufficient to support a buffering reaction in the ECA product solution and prevent the pH from being too low or too high. In embodiments, the pH of the HOCl ECA product solution is maintained between pH 5.5 and pH 7.2 by the buffering reaction. In an embodiment, the ratio is 96% NaCl to 4% citric acid. For example, as the ECA production solution acidifies, $Cl_2$ may bubble out of solution and lower the FAC concentration. When the solution of sodium chloride and citric acid is exposed to the electrodes of the ECA system 1000, an electrolysis reaction occurs. Electrolysis of the sodium chloride may produce at least hypochlorous acid, which is a mild acid that, depending on the circumstances, has sanitizing properties, disinfectant properties, antimicrobial properties and the like. Other chloride containing species are also possible products of the electrolysis reaction. Further, sodium hydroxide (NaOH) may be produced by the electrolysis reaction. Various other components and gases may also be produced by the electrolysis reaction, such as chlorine gas ($Cl_2$), hydrogen gas ($H_2$), oxygen ($O_2$), and, when water ionizes, ozone ($O_3$). Ozone itself may act as an antimicrobial and/or disinfectant. In embodiments, the oxygen being released may saturate the aqueous solution so that it may act as an antimicrobial agent.

In certain embodiments, the reactant salt is sodium chloride alone without any citric acid.

The product solution of hypochlorous acid may exhibit a pH in the range of 3 to 7. In certain embodiments, the ECA product solution of hypochlorous acid may exhibit a pH in the range of 5-7. In embodiments, the relative concentration of NaOH and HOCl in the ECA product solution is 85% HOCl to 15% NaOH. Depending on the operational parameters of the particular apparatus and user requirement, the product solution of hypochlorous acid may exhibit an FAC in the range of 20 ppm-1000 ppm. For example, hypochlorous acid produced at FAC's of about 100-200 ppm are suitable for basic sanitizing while higher FAC's, such as about 1000 ppm, are useful in disinfecting, anti-microbial applications and hospital sanitizing applications. Thus, operation of the ECA system 1000 embodied in any apparatus where the reactant solution includes sodium chloride, and optionally citric acid, may result in a sanitizing solution or an antimicrobial/disinfecting solution depending on the operation parameters of that apparatus, as described herein. Once electrode activation has terminated, the ECA product solution may have a stable shelf life. For example, the HOCl ECA product solution may have a shelf life of 30 days. In another example, the HOCl ECA product solution may have a shelf life of up to 60 days. As such, the ECA system 1000 can provide a stable output of 100 ppm to 1000 ppm HOCl that has significant shelf life, enabling the ECA product solution to be bottled and used at a later date or sold. Both sanitizing solutions wherein the FAC is at or below 200 ppm FAC and disinfecting solutions where the FAC is over 200 ppm can be stable outputs of the ECA system.

In some embodiments, halide salts or metal halide salts, such as sodium bromide (NaBr) or potassium bromide (KBr) or iodine salts, may also be used in the ECA system.

In embodiments, the reactants may be pigmented to indicate the identity of the reactants. In embodiments, the pigments used may be selected to match the international training symbols for the particular kind of solution being generated.

In an embodiment, a possible electrolysis reaction that occurs is: $2NaCl + 2H_2O \Rightarrow Cl_2 + H_2 + 2NaOH$. The reaction can also be considered as following: $2Cl^- + 2H_2O \Rightarrow Cl_2 + H_2 + 2OH^-$. A further reaction may occur with the products of this initial reaction: $Cl_2 + OH^- \Rightarrow HOCl + Cl^-$. The directions and equilibrium points of these reactions will depend on the reaction conditions and may be controlled by the control module 1010.

In another example, the starting material for the ECA system 1000 is potassium carbonate. When the solution of potassium carbonate is exposed to the electrodes of the ECA system 1000, an electrolysis reaction occurs. Electrolysis of the potassium carbonate produces at least potassium hydroxide, in certain embodiments in a mild alkaline solution that is useful as an environmentally friendly cleaner or degreaser. Other potassium containing species are also possible products of the electrolysis reaction. Various other components and gases may also be produced by the electrolysis reaction, such as hydrogen gas, oxygen, and ozone. Various carbonate salts may be present in solution. The product solution of potassium hydroxide may exhibit a pH in the range of 7.5 to 11.2, or possibly higher or lower. Thus, operation of the ECA system 1000 embodied in any apparatus where the reactant solution includes potassium carbonate may result in a cleaning solution depending on the operation parameters of that apparatus, as further described herein. Once electrode activation has terminated, the product solution may have a shelf life of 2 to 14 days. As such, the ECA system 1000 can provide a stable output of KOH that has significant shelf life, enabling the ECA product solution to be bottled and used at a later date or sold. Both cleaning solutions wherein the hydroxide ion concentration is at or below 6 mM and degreasing solutions where the hydroxide ion concentration is above 6 mM can be stable outputs of the ECA system.

In an embodiment, a possible electrolysis reaction that occurs is: $K_2CO_3 + H_2O \Rightarrow 2\ KOH + CO_2$.

Potassium carbonate may be referred to as a carbonate salt or a metal carbonate salt. Other members of the periodic family may be used in place of the potassium to form a reactant used in the ECA system. For example, sodium carbonate ($Na_2CO_3$) or sodium bicarbonate ($NaHCO_3$) may also be used in the system. In embodiments, the reactants may be pigmented to indicate the identity of the reactants.

KOH in solution may react with the grease and oils in oily dirt during cleaning. Since grease and oil contain lipids, the KOH reacts with them to undergo saponification in which a non-polar lipid molecule is attached to an $OH^-$ radical. The non-polar end of the molecule dissolves in the non-polar grease, while the polar $OH^-$ radical is attracted to the water molecules. This allows the complex to remain suspended in the water allowing grease and oily dirt to be washed into the liquid and removed during cleaning/degreasing. In other embodiments, micelles or hydrophobic-hydrophilic interactions may be involved in the cleaning/degreasing mechanism.

In yet another example, the starting material for the ECA system 1000 is water, such as municipal water, so long as the water contains trace quantities of salts sufficient to initiate an electrolysis reaction in the water. When the trace-containing water is exposed to the electrodes of the ECA system 1000, an electrolysis reaction occurs. Electrolysis of the water produces at least hydrogen ions ($H^+$) and hydroxide ions ($OH^-$). Hydronium ions ($H_3O^+$) may also be produced. In this example, continuous electrode activation is required to maintain the electrochemical activation of water as the disassociated water radicals can only exist for a short period of time before re-associating back into water molecules once the power is turned off and the electrodes are de-activated. However, if they are used in the dissociated state, the cleaning and other properties of ionized water may be realized. Such electrochemically activated water is useful in many applications, as described herein.

Certain of the embodiments described herein produce one or more of sanitizers, cleaners, antimicrobials, disinfectants and degreasers. Certain embodiments, such as the Medical Receptacle Design, are more particularly designed to produce a high FAC concentration disinfectant; however other embodiments described herein may also produce disinfecting solutions.

Figure 3:
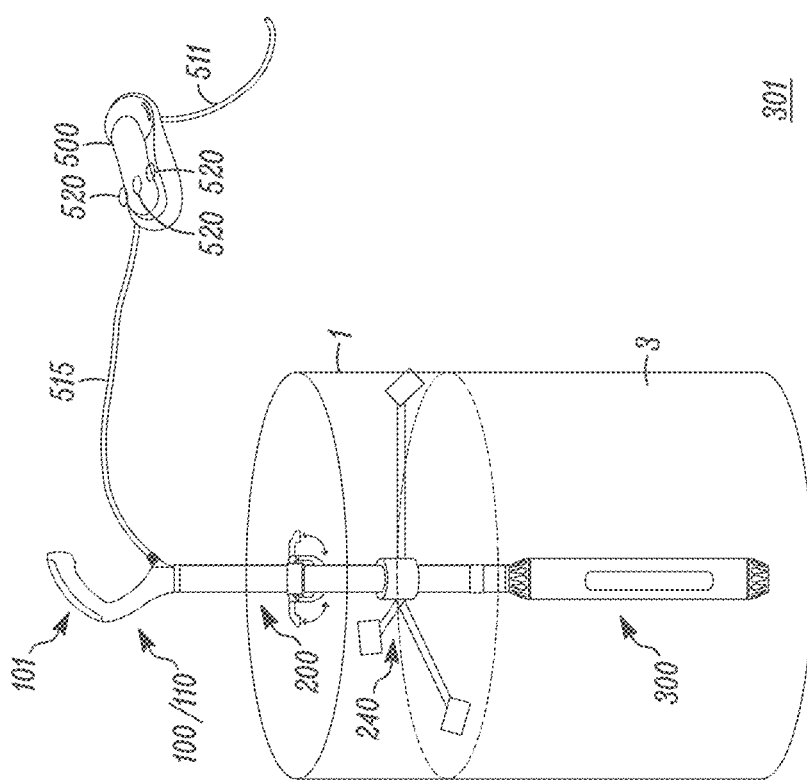
FIG. 3 depicts an elevational view of an embodiment as it would appear in use.

FIG. 3 shows one embodiment of a system 301 for electrochemically activating water. Here, an immersion wand 101, also described herein as an elongated immersive apparatus, has an immersion head 300 that is adapted to be immersed in an aqueous salt solution 3 in container 1. In some embodiments, additional substances may be added such as small amounts of citric acid.

The immersion wand 101 may optionally include an extendable shaft 200 that connects immersion head 300 with a handle 100. The extendable shaft 200 has an upper shaft 210 which may telescope from the lower shaft 230 resulting in an adjustable length shaft.

An adjustable fastener 220 secures upper shaft 210 relative to lower shaft 230 to keep the extendable shaft 200 at a desired length.

A stabilizer assembly 240 connects to the extendable shaft 200 of immersion wand 101, connected to and extending from, the immersion head. The stabilizer assembly 240 holds the immersion wand 101 in a vertical position generally in the center of container 1.

The solution 3 is an aqueous salt solution which may include common, non-toxic salts such as sodium chloride (NaCl), Potassium chloride (KCl), and potassium carbonate ($K_2CO_3$) or other salts, as described herein.

A base unit 500 is connected to the immersion wand 101 through an umbilical 515 which provides electrical power to electrodes (not shown here) in immersion head 300. Base unit 500 controls the system.

Base unit 500 has a user interface to allow a user to select varying amounts of electrical power to be provided to the immersion head 300. In one embodiment, the power selection controls 520 includes at least three buttons indicating a low output for the first button, a medium output for the second button, and a high output for the third button.

These three buttons indicate varying amounts of time that power would be provided to immersion head 300, wherein the high output indicated by the third button would result in additional power being provided to the immersion head or power being provided for a longer period of time than it would be if the first or second buttons were selected. In other embodiments, buttons may be provided for varying the properties of the electrical power (such as current and voltage) applied to the solution.

For example, in a 3-stage power setting: low would apply to creating cleaning fluid for mop buckets and small use cleaning amounts. This would be approximately 2 to 4 minutes of power provided to the immersion head 300.

For medium amounts, for use in midsized power equipment carpet extractors, automatic scrubbers, or larger cleaning buckets, a brewing time of 4 to 6 minutes would be performed.

For large powered cleaning equipment and industrial cleaning needs, the power would be provided for 7 to 9 minutes.

Figure 4:
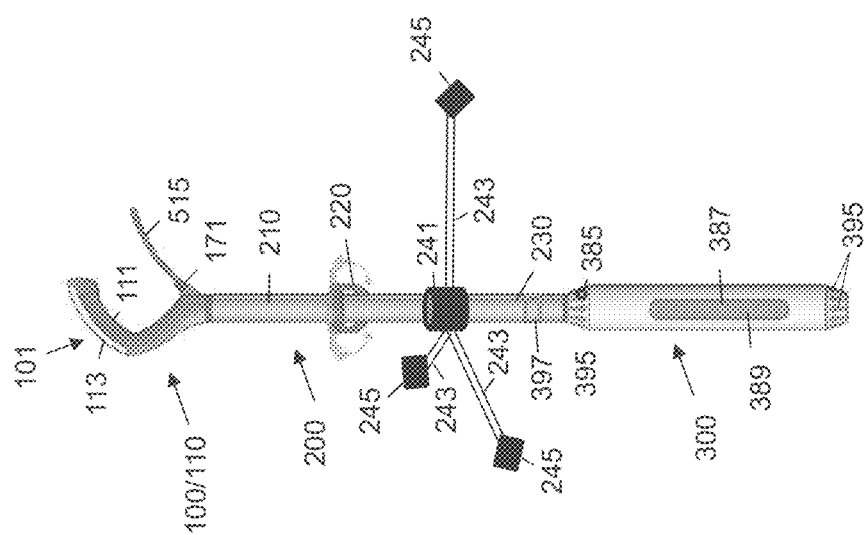
FIG. 4 depicts an elevational view of the immersion wand of FIG. 3 with stabilizer assembly.

FIG. 4 depicts an elevational view of the immersion wand of FIG. 3 with stabilizer assembly. The stabilizer assembly 240 includes a collar 241 which may be slidingly attached to the extendable shaft 200. Radiating from the collar 241 are stabilizer arms 243 having adjustable connectors 245 on their peripheral end. The adjustable connectors 245 are designed to removably attach to a container (1 of FIG. 3) into which it is placed. The stabilizer arms may also be extendable to accommodate different sized containers. Alternatively, the adjustable connectors 245 may not be required if the stabilizer arms 243 are long enough to rest on the top edge of the container.

Figure 5:
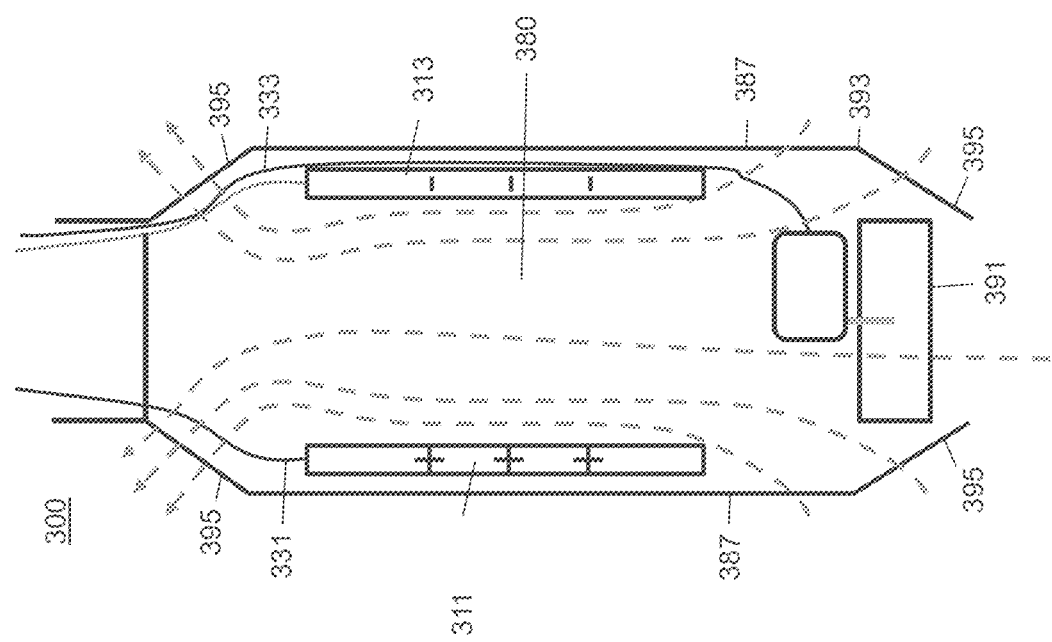
FIG. 5 shows the inside chamber of the immersion head 300.

Referring now to both FIGS. 4 and 5, an impeller 391 draws the solution into the immersion head 300 through the bottom of the immersion head 300, the lower end ports 395 and side ports 387 and through an internal chamber 380. Internal chamber 380 includes electrode chips 311, 313 positioned on either side of the internal chamber 380, typically about eight (8″) inches from the bottom of the immersion head 300. When the electrode chips 311, 313 are provided with a proper amount of electric power, the electrode chips 311, 313 cause electricity to pass through the solution in the internal chamber 380, electrochemically activating the solution to create an ECA product solution.

The ECA product solution is then expelled back out of internal chamber 380 of the immersion head 300 through upper end ports 395 to be mixed with the solution 3 in container 1.

Figure 6:
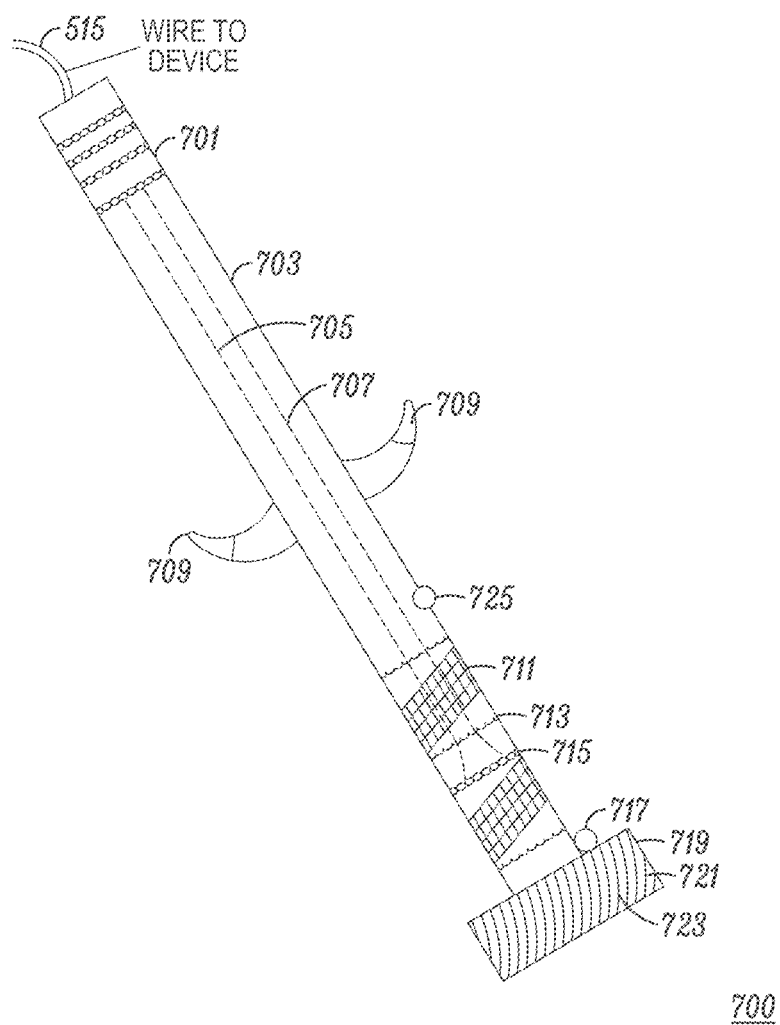
FIG. 6 shows an alternative embodiment of an immersion wand.

FIG. 6 shows an alternative embodiment of an immersion wand. This includes an upper housing 703 which has a 2 inch to 2.5 inch diameter, in this embodiment. A top end of the upper housing 703 has a rubber grip 701 that acts as a handle.

A pair of power supply lines 705, 707 run through the center of the upper housing 703 and connect to electrodes 713, 715, respectively.

The upper housing 703 connects to a wider lower housing 719 that encloses submersible circulating fan 721. Lower housing 719 includes openings to allow a fluid, such as an aqueous solution, to enter and pass through a portion of upper housing 703, past electrodes 713 and 715. This requires the lower housing 719 and a portion of upper housing 703 to be submerged in the aqueous solution.

The aqueous solution enters through the screen 723 covering the openings in the lower housings 719 and exits through openings in the upper housing covered by protective screen 711. The submersible circulating fan 721 draws the water in through the lower housing 719 and causes it to flow past the electrodes 713, 715 and out of the openings and screen 711.

A power consumption LED 717 is located on the upper side of the lower housing 719 and illuminates when power is being supplied to the immersion wand 700.

It is to be noted that the immersion wand design may be employed in water without adding any salts or other additives. Therefore, a cleaning device in which the immersion wand design is present and operating in the solution as it is being used would be beneficial. This would be the case of a floor or carpet cleaning machine which has its own 12 VDC power supply. The immersion wand device can be placed in the cleaning solution receptacle and it can operate continuously as the machine cleans the floor or carpet. Similarly, it could be used on riding cleaners or scrubbers to produce a cleaner, but with no harmful byproducts.

FIG. 7 shows an alternative embodiment of the handle 100 being a loop handle 130. Loop handle 130 has a circular loop design within the inner loop grip 131. Loop handle 130 also includes indicator lights 113 on its outer side to indicate operation of the device. It includes an exit port 171 where the umbilical 515 from the immersion head exits the loop handle 130.

FIG. 8 shows another alternative embodiment of the handle 100 of the present invention, that is a straight handle 150. As with the other embodiments of the handle 100, the umbilical 515 exits the handle at the exit port 171.

Figure 8A:
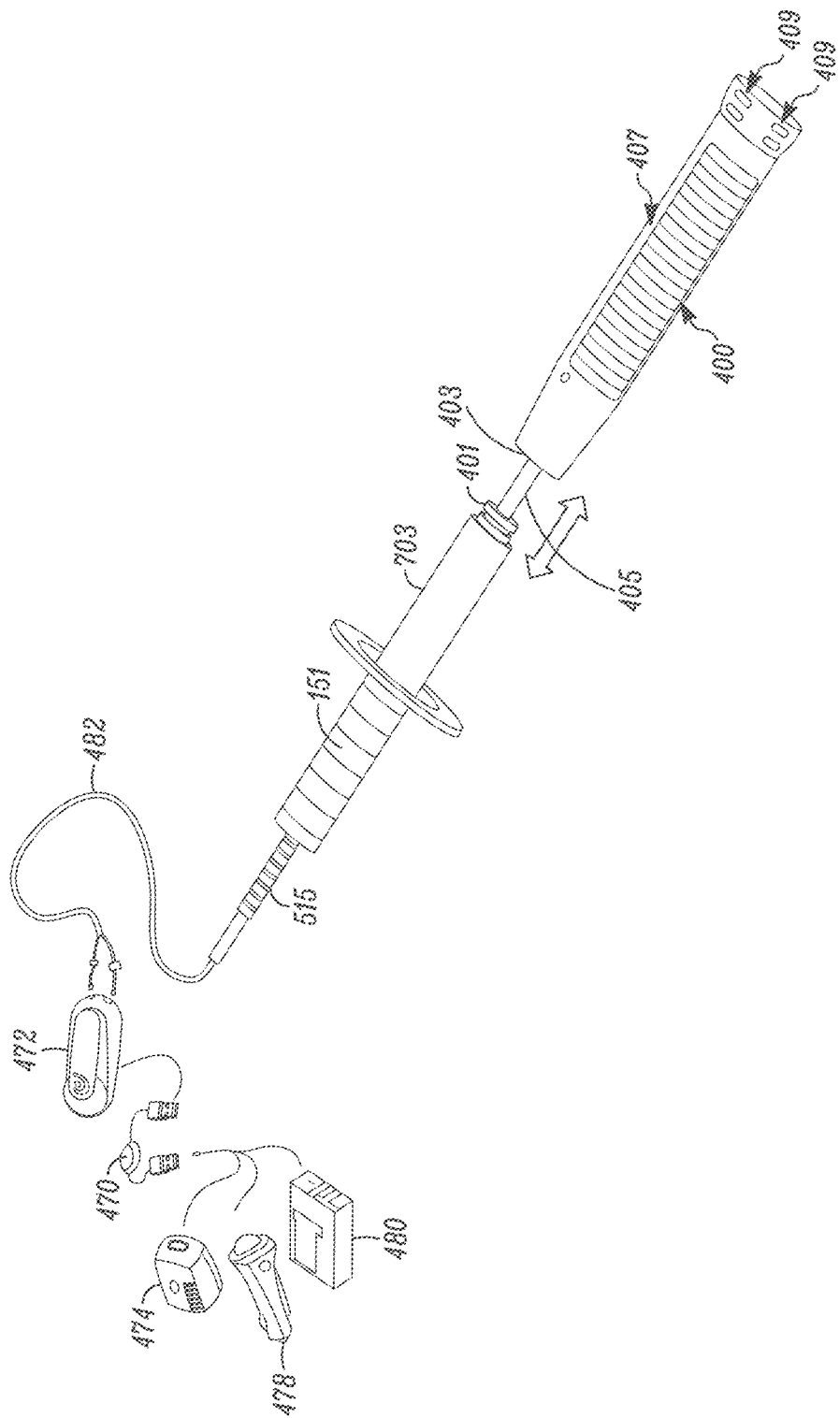
FIG. 8A depicts a perspective view of another embodiment, showing an extendable immersion head design.

FIG. 8A shows another alternative embodiment of the present invention that includes an immersion head 400 that detaches from an upper housing 703. The immersion head 400 is attached to the remainder of the device by an extension rod 405. This arrangement allows the immersion head 400 to adjust to extend to the bottom of a large container, while still being able to retract to fit into smaller containers.

A first part of a fastener 401 is attached to the lower part of the upper housing 703. The second part of the fastener 403 is attached to the top of immersion head 400. When retracted the first part of the fastener 401 and the second part of the fastener 403 attach to each other holding the immersion head 400 in its retracted position. In the embodiment shown, the fastener used is a twist lock-type fastener in which the first part 401 and second part 403 of the fastener are pushed together then twisted to lock. To unfasten them, it is twisted in the opposite direction then pulled apart.

This embodiment shares the same straight handle 151 and umbilical 515 as the embodiment of FIG. 8. In FIG. 8A, the umbilical 515 presents a cord 482 that connects to a control module/air pump 472 to receive both air and power.

In this embodiment, vanes 407 or louvers are employed instead of screens (as shown in previous embodiments). The vanes or louvers allow gas bubbles produced during the ECA to be more easily released from the interior of the wand. In certain embodiments, the louvers may be opened or closed. In certain embodiments, the control module 1010 may control the degree to which the louvers are opened or closed.

This embodiment employs an air pump, similar to air pump 1012 described in connection with FIG. 3. The air bubbles escape from the air pump venting chamber 409 and agitate the solution causing mixing of the solution and any undissolved reactants or additives.

Figure 8B:
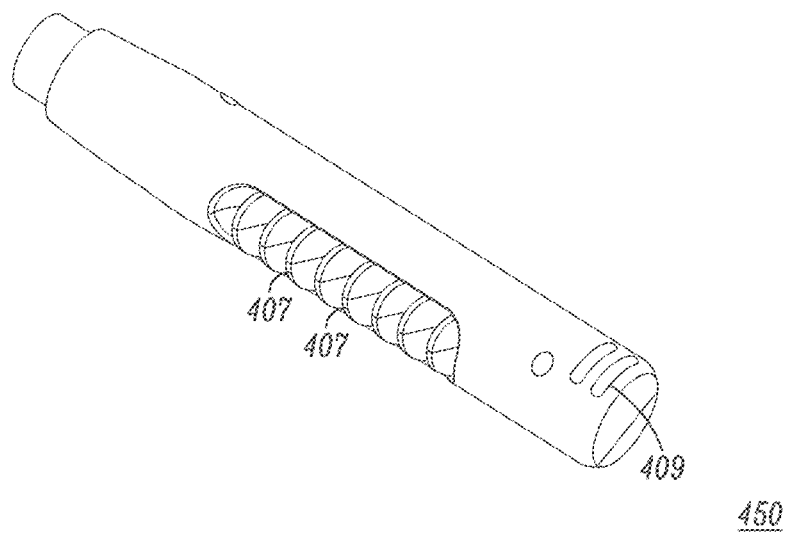
FIG. 8B depicts a perspective view of another embodiment of the immersion heads.

FIG. 8B is a perspective view of another embodiment of an immersion head 450, similar to that shown in FIG. 8A. As with the previous embodiment, it employs vanes 457 or louvers to direct escaping bubbles and the solution out of the immersion head 450. It also includes an air pump venting chamber 459 for the release of air pumped down through the immersion head 450 by an air pump, similar to air pump 1012 of FIG. 3.

Figure 8C:
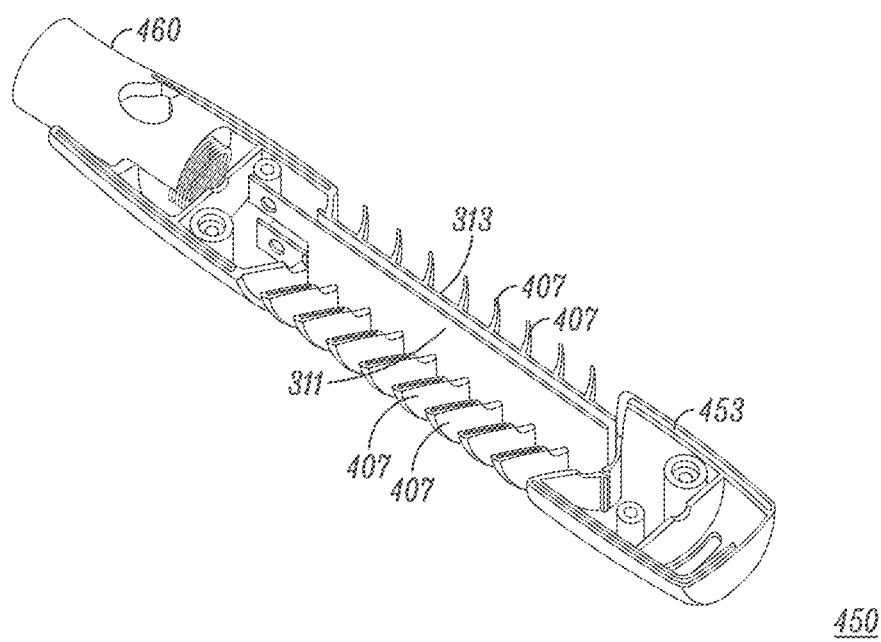
FIG. 8C depicts a view of the immersion head design of FIG. 9B with the top housing removed.

FIG. 8C is a view of the immersion head of FIG. 8B with its upper housing 451 removed. The lower housing 453 is shown holding the internal structures in place. The parallel generally rectangular electrodes 311, 313 are positioned at the center of the lower housing 453. An extension support assembly 460 receives and secures an extension rod, similar to extension rod 405 of FIG. 8A.

Figure 8D:
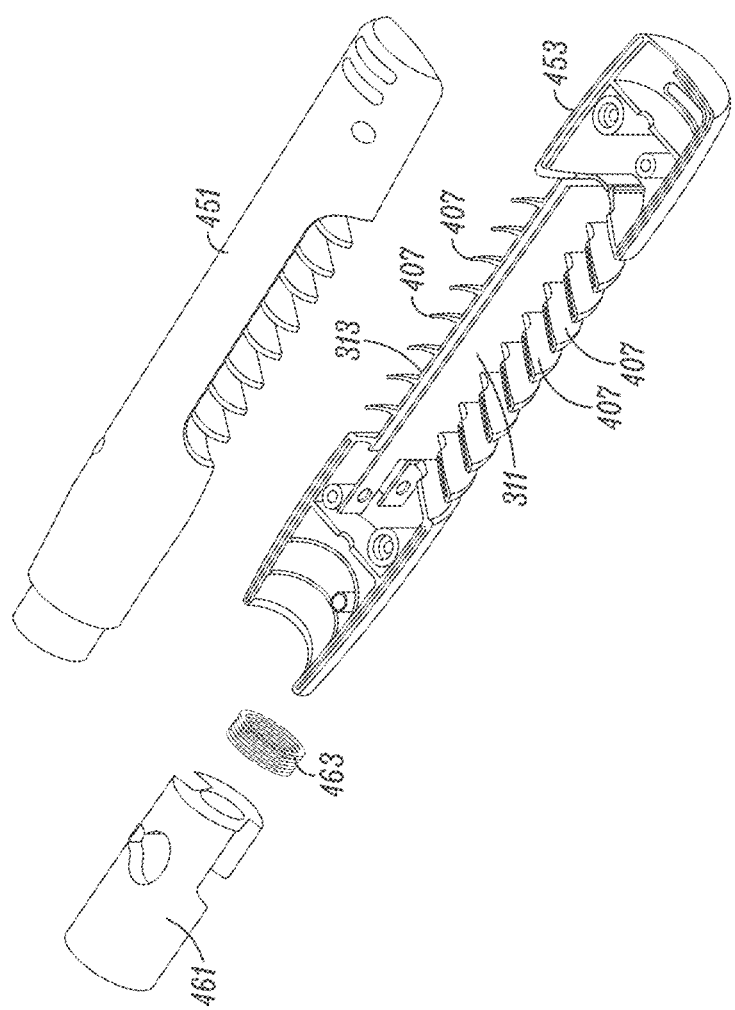
FIG. 8D depicts an exploded view of the immersion head of FIG. 9B.

FIG. 8D is an exploded view of the immersion head 450 of FIG. 8B. Here the extension support 460 is shown to be constructed from an extension support collar 461 which fits inside of an extension support body 463.

Figure 9:
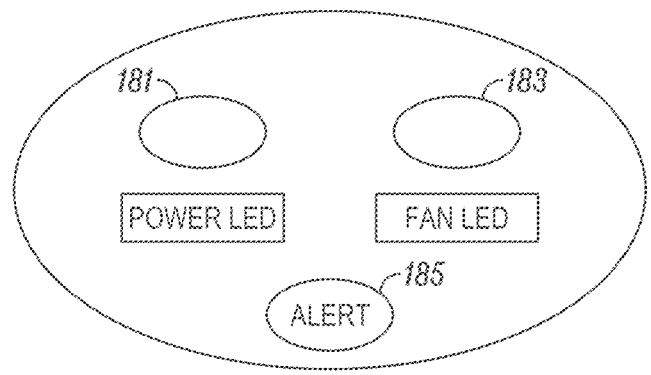
FIG. 9 depicts an enlarged view of the top of the handle 100 of the immersion wand.

FIG. 9 is an enlarged view of the top of the handle 100 of the immersion wand. It includes a power LED 181 that is lit when power is provided to the immersion head 300. A fan LED 183 is lit when the fan (impeller) in the immersion head 300 is operating. An alert LED 185 is lit when the device senses a power failure, such as a low voltage. In other embodiments, various displays and indicators may be provided to provide information regarding various properties of the device, solution and process. For example, a timer may provide the time remaining and a screen may provide the pH of the solution and the level of salt remaining.

Figure 10:
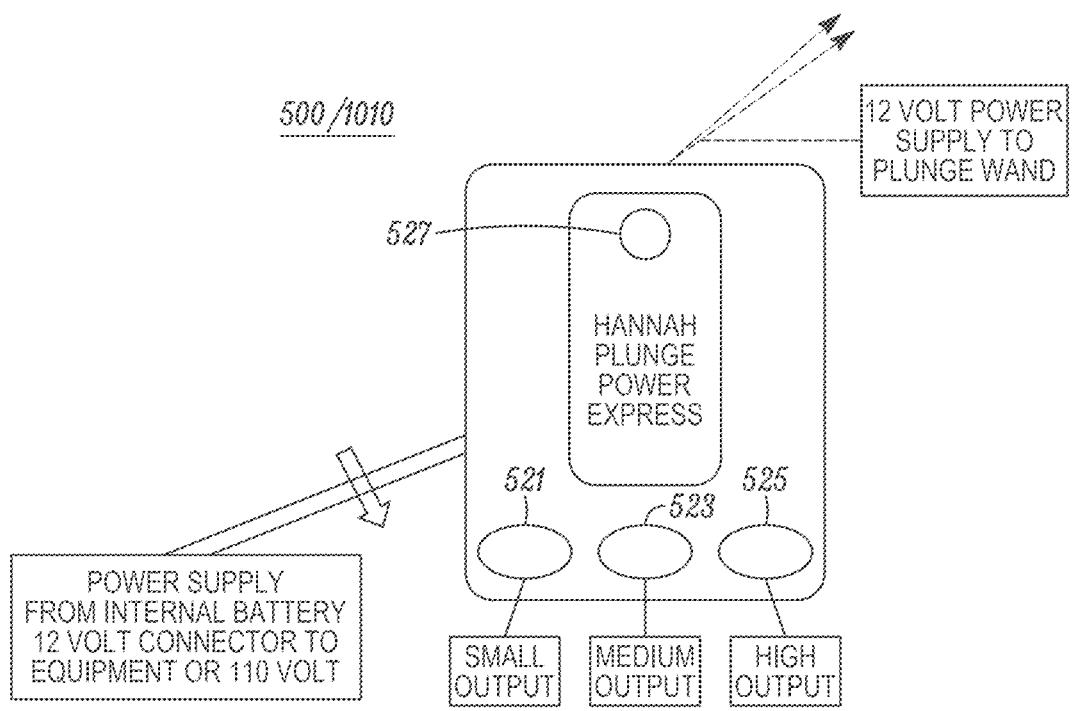
FIG. 10 depicts an enlarged view of the base unit 500.

FIG. 10 is an enlarged view of the base unit 500 which operates in a similar manner as the control module 1010 of FIG. 3. In this embodiment, an operator can select one of three buttons, low output 521, medium output 523 or high output 525 depending upon the strength of the cleaning fluid required. Base unit 500 also has a power confirmation LED 527 which flashes indicating that power is being transmitted to the immersion head 300. The base unit 500 is equipped with a time and the ability to start and shut off power to the immersion wand or the Power Disc. It also may include logic to determine when there is not enough power and light the Power LED.

When the power is operating correctly, it flashes the Power LED 181.

The base unit 500 is connected to and able to receive input from liquid sensor 397 of immersion wand 101, and liquid sensor 725 of the second embodiment of the immersion wand 700. These indicate when there is enough aqueous solution to cover the functional portion of the immersion wand. The base unit 500 will only supply electrical power when the liquid sensors indicate that there is enough solution.

The base unit 500 also has the ability to reverse polarity of the power being sent to the chips (electrodes). The reversal of polarity allows charged particles that migrate to one or the other electrode to be removed from the electrode. This is an effective way of cleaning the electrodes.

The immersion wand is designed to be inserted into a number of different receptacles to operate and produce an ECA product solution. It can be used in tanks, mop buckets, jugs, bottles, and other devices and containers that hold water.

In addition, due to its compact design it may be inserted into a receptacle of an existing carpet scrubber, power floor scrubber, or other existing cleaning or sanitizer equipment.

In another embodiment, the immersion wand design operates off of a 12 V DC car voltage. In this embodiment, it can be inserted into a cleaning solution reservoir of a riding floor scrubber to create the ECA product solutions. It would be powered from the 12 V DC system of the riding floor scrubber.

The embodiments described herein may produce a sanitizer, disinfectant, glass cleaner, general purpose cleaner, heavy duty cleaner and degreaser for use in a variety of devices and applications, including power scrubbers, and carpet extractors.

Figure 10A:
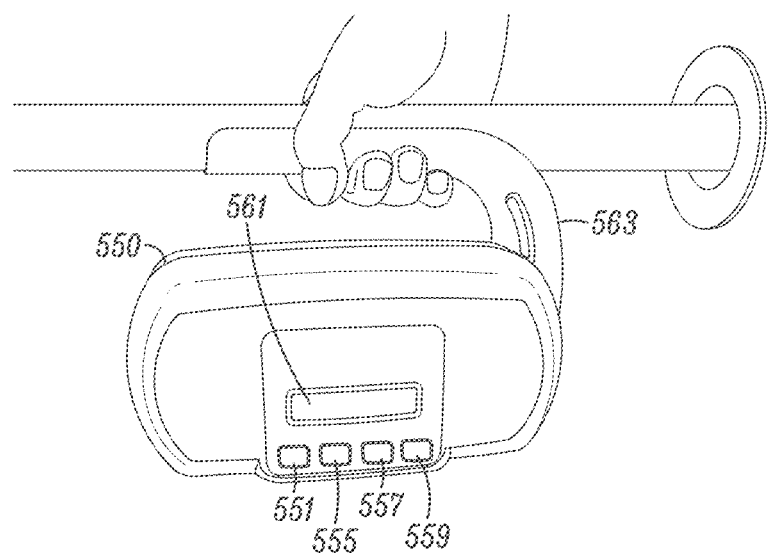
FIG. 10A depicts another embodiment of a base unit 500.

FIG. 10A shows another embodiment of a base unit 550. This functions in a similar manner as base unit 500 shown in FIG. 10, but includes a continuous use button. Instead of having three different levels of output, the embodiment of FIG. 10A has a low output button 551 that may function the same as button 521 of FIG. 10, a high output button 559 that may function the same as 525, but includes a continuous use button 559 which may cause the power to be continuously applied to the electrodes. This is typically used to ionize water. The naturally occurring solutes allow the current to pass between the electrodes ionizing water. The ionized water is intended to be used immediately, before it re-associates back into water.

In this embodiment, the handle 563 has a concave shape allowing the wand that is used with this embodiment to snap into the concave handle allowing the user to easily carry both with one hand.

Figure 11C:
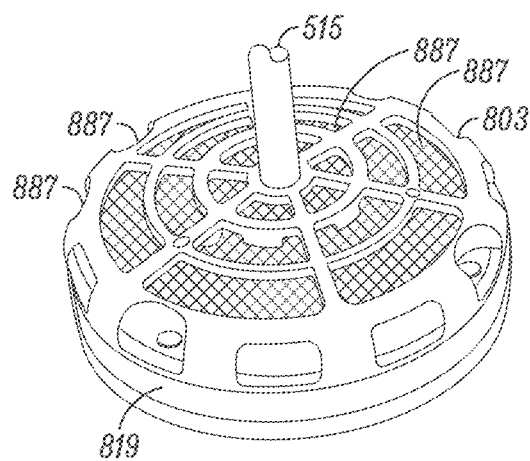
FIG. 11C depicts a perspective view of another embodiment similar to that shown in FIGS. 11A and 11B.

FIG. 11A, FIG. 11B, and FIG. 11C show still another embodiment of the ECA system, embodied as an immersive apparatus. It includes all of the functional parts as the immersion wand designs, but physically has a much lower elevational height. It is designed to be fully immersible and fit in a bucket in a solution and operates to activate a salt water solution to create sanitizer and/or detergent solutions.

Here it is shown that the solution enters through ports 887 of a lower housing 819 drawn in by an impeller (not shown). The solution passes through an internal chamber having electrode chips that electrochemically activate the solution.

The electrochemically activated solution then passes out of ports 887 of the upper housing 803. A power consumption LED lights when the device is in operation.

The immersive apparatus may be capable of running on 12 volt power and may have an LED built into the disc to confirm operation of Clean Disc when submerged. The immersive apparatus may be tied into GFCI for safety when in operation and may employ larger power chips for maximum operation.

In embodiments, the Immersion Wand Design or Immerse-A-Clean may reverse polarity every 2 minutes and rest after 2 minutes for 30 seconds.

In embodiments, the Immersion Wand Design may provide between 8 and 15 amps of current to the solution in a receptacle depending upon the amount of solution to be activated and the concentration of salts in solution.

In embodiments, the Immersion Wand Design when ionizing water may be continuously operating. The Immersion Wand Design may also have a 2 minute cycle time and 10 minute cycle time for producing sanitizing and cleaning solutions.

In embodiments, the Immersion Wand Design may utilize flat, rectangular electrodes.

In embodiments of the immersion wand design, various starting concentrations of reactants may be used. For example, 3-12 g of NaCl may be added to a ½ gallon of water. In other words, concentrations ranging from 36 mM to over 100 mM of NaCl may be used as a starting solution. More particularly, a smart chlorine solution may utilize 12 g NaCl in a ½ gallon of water to provide approximately 108.5 mM NaCl. In another example of a general purpose cleaner, 4 g of potassium carbonate may be added to a half gallon of water to provide approximately 15.3 mM potassium carbonate to start. Heavy duty cleaners and degreasers may utilize additional potassium carbonate such as to provide approximately 23 mM to start.

All the elements of the above described embodiments may be incorporated into other self-contained or other embodiments.

Embodiments of the ECA system may have a housing, such as housing 1002, that is constructed from a non-conductive plastic that is bis-phenol A (BPA)-free.

The immersion wand may include a clip to be attached to powered equipment to hold the immersion wand and to allow on board use.

A power LED lamp may be included on the bottom of wand to assure user of its operation. One or more LEDs on the handle may light to confirm operation of wand when submerged.

A wet detection/moisture sensor may operate to insure that there is no operation unless the device, or at least the electrodes, is submerged.

The base unit may contain one or more circuit cards with timers and ground fault circuit interrupter (GFCI) to ensure user safety.

The wand length may be adjustable to set depth in water and user needs.

Another embodiment of the ECA system 1000 is the electrode-integrated receptacle apparatus. All of the electrode-integrated receptacle apparatus described herein, such as the Portable Receptacle, Enlarged Receptacle and Medical Receptacle Designs, can be used as table top units with circular, flat electrodes. One embodiment of the electrode-integrated receptacle apparatus 1200 is shown in FIG. 12. The embodiment in FIG. 12 is referred to as the "Trio™" design. In this embodiment, the electrodes 1204 are disposed within a receptacle 1202 that serves as a reservoir for the input of water or a reactant salt-containing solution 1214. In this embodiment, the electrodes 1204 may resemble flat circular plates or grids, such as those shown as circular electrodes 1102 in FIG. 2. In this embodiment, the electrodes are placed horizontally and parallel to each other. A spacer is designed to keep these electrodes a specific distance apart.

The receptacle 1202 is designed to fit into the base 1208. The electrical contacts on the base 1208 make contact with receptacle contacts 1226 on the bottom of the receptacle 1202 that connect to the electrodes 1204. When the receptacle 1202 is properly placed on the base 1208, power from a power supply 1210 is passed through the contact of the base 1208, into the receptacle 1202 and to the electrodes 1204. The electrical power provided causes an electrolysis reaction, such as any of those described herein to occur in the receptacle 1202. The base 1208 or the receptacle itself 1202 may have a display, such as a digital readout or digital user interface 1212 to indicate various parameters of the operation of the electrode-integrated receptacle apparatus 1200.

Figure 12A:
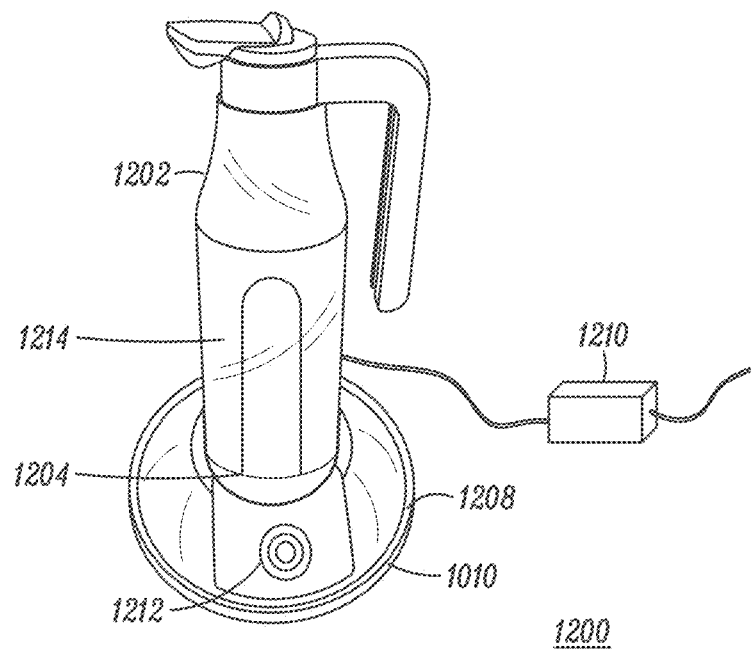
FIG. 12A depicts a perspective view of an embodiment consistent with the schematic of FIG. 12.

FIG. 12A is a perspective view of an embodiment of the apparatus consistent with the schematic of FIG. 12. FIG. 12A shows the electrode-integrated receptacle 1200 in its base 1208 operating to produce an ECA product solution. In this embodiment, a light underneath the receptacle lights when the solution is being created.

Figure 13:
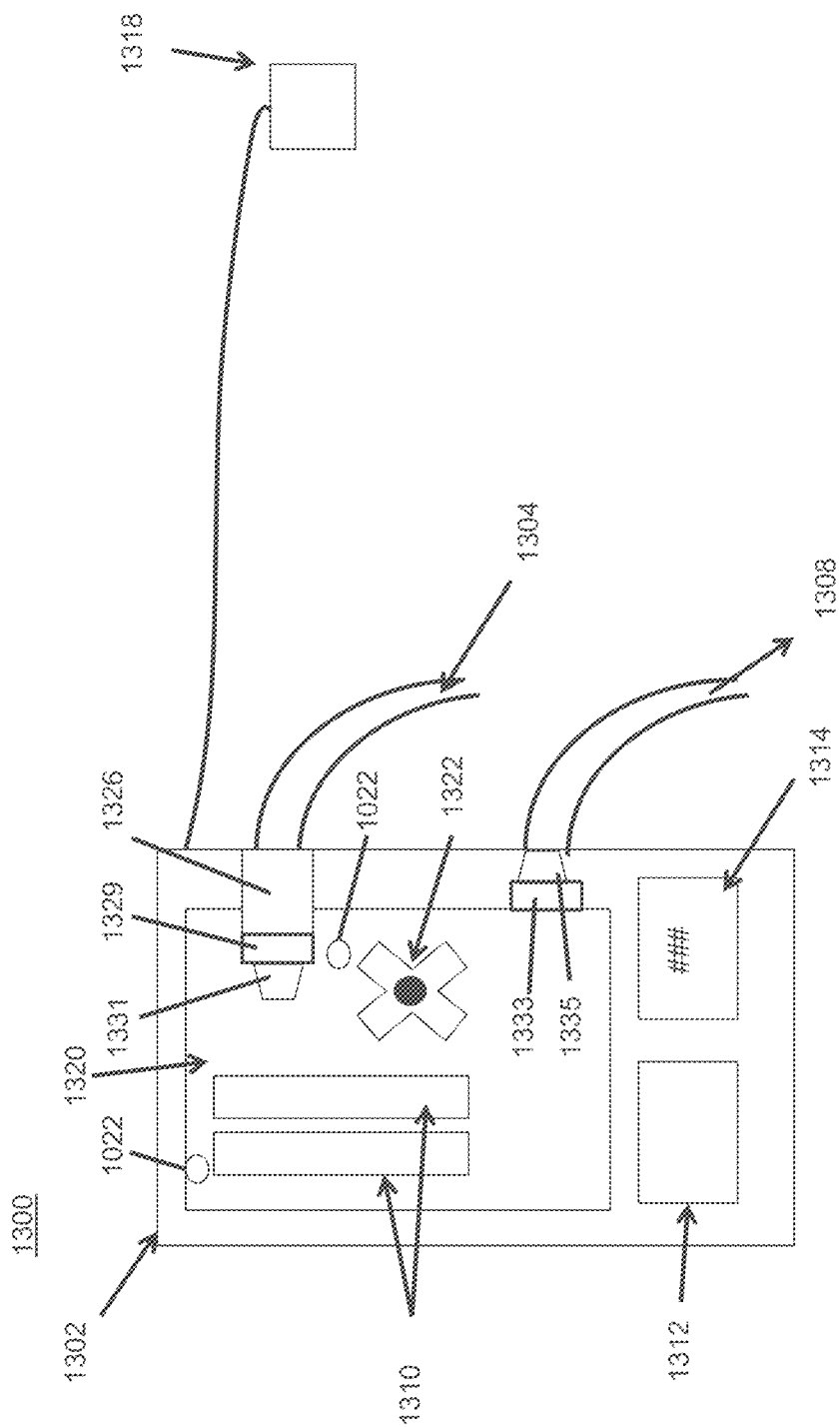
FIG. 13 depicts an instant flow apparatus.

Also note that the digital UI 1212 shows a number of indicator lights. The UI 1212, as described herein, may be controlled by the control module 1010 which is integrated into base unit 1208. This same operation may also be used on the other embodiments such as that shown in FIG. 13.

Figure 12B:
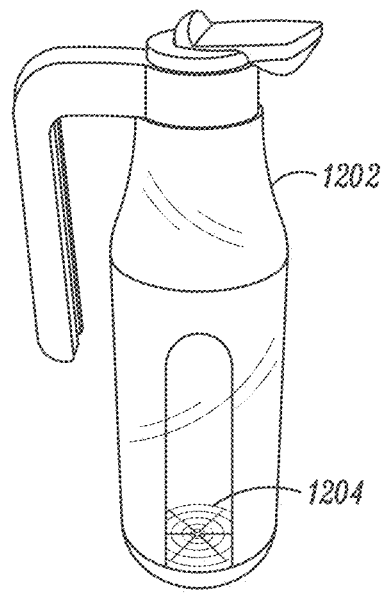
FIG. 12B depicts a perspective view of the receptacle of the embodiment shown in FIG. 12A.

FIG. 12B is a perspective view of the receptacle 1202 of the embodiment of the present invention shown in FIG. 12A.

Figure 12C:
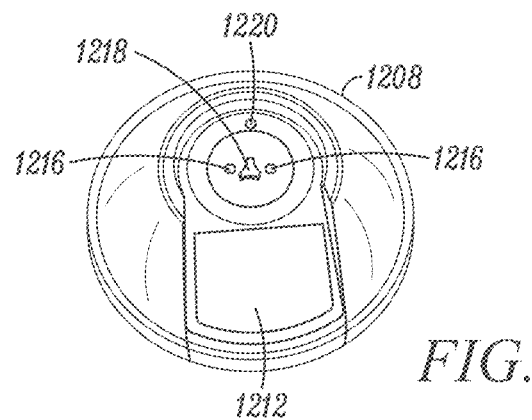
FIG. 12C depicts a perspective view of the charging base receptacle of the embodiment shown in FIG. 12A.

FIG. 12C is a perspective view of the base 1208 of the embodiment of the present invention shown in FIG. 12A. In this view, the electrical contact 1216 can be seen that make contact with those of the receptacle 1202 when it is placed on the base 1208. An alignment feature is either a protrusion or a recess that has a complementary shape on the receptacle 1202 causing it to align the receptacle 1202 in the proper location and orientation to have the electrical contacts 1216 meet those of the receptacle 1202.

The digital UI 1212 can easily be seen. It is driven by the control module 1010 and may provide any number of indications or prompts to a user, as described herein.

Figure 12D:
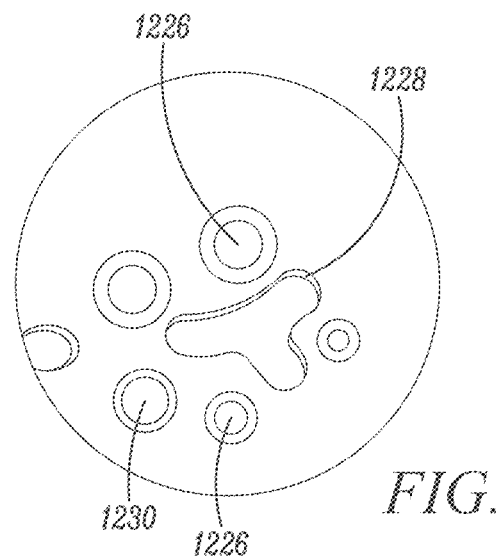
FIG. 12D depicts a plan view of the bottom of the receptacle of FIG. 12B.

FIG. 12D shows the bottom of the receptacle 1202. The receptacle contacts 1226 are visible. These are sized and positioned to touch the electrical contacts 1216 on base 1208 when the receptacle 1202 is properly positioned on the base 1208. The receptacle alignment feature 1218 on the base 1208 is the complement of the alignment feature 1228 on the bottom of the receptacle 1202 causing them to fit together when the receptacle 1202 is properly placed on the base 1208. A magnet 1230 in the receptacle 1202 lines up with a magnet sensor 1206 in the base 1208. The control module 1010 identifies when the magnet sensor 1206 senses magnet 1230 indicating that the receptacle is properly positioned on the base 1208. Power is provided when the receptacle is on the base 1208, and is not provided once the receptacle 1202 is removed.

Figure 12E:
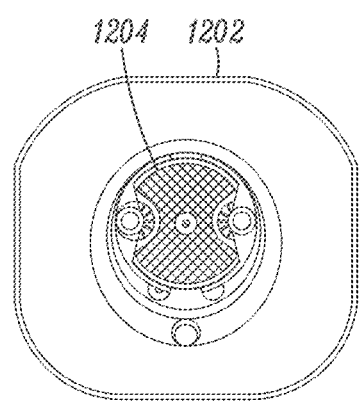
FIG. 12E depicts a sectional view of the receptacle of FIG. 13B viewing the bottom of the receptacle.

FIG. 12E is a sectional view of the receptacle of FIG. 12B viewing the bottom of the receptacle. In this view the electrode 1204 is visible indicating its circular shape and that it is positioned parallel to the bottom of the receptacle 1202.

In embodiments, the receptacle can hold 40 ounces of solution, the current flow is reversible at the halfway point during the 5 minute cycle, the operating amperage is 4 amps, the operating voltage ranges from 110 to 240 volts, and the narrowing shape of the receptacle ensures proper mixing.

In embodiments of the portable receptacle design, various starting concentrations of reactants may be used. For example, 3 g of NaCl may be added to 40 ounces of water to provide approximately 43.5 mM NaCl. In another example of a general purpose cleaner, 0.75 g of potassium carbonate may be added to 40 ounces of water to provide approximately 4.6 mM potassium carbonate to start. Heavy duty cleaners and degreasers may utilize additional potassium carbonate (e.g. 2 g) such as to provide approximately 12.3 mM to start.

Another embodiment of the electrode-integrated receptacle apparatus 1200 is referred to as the Medical Receptacle Design or the "Trio Rx™" design. This is similar to the apparatus 1200 described herein, but is designed to produce disinfecting solutions having up to 1000 ppm of FAC. This is intended for medically-related disinfecting applications. The higher FAC is effective against many common microbes including Methicillin Resistant microbes (MRSA). The medical receptacle design is intended to use more NaCl and receive additional electrical power from the electrodes as compared with the portable receptacle design.

To dissolve the larger amount of salt, the Medical Receptacle Design may further include an impeller, as described herein, in the receptacle 1202 that rotates to agitate the salt. The impeller may be in the form of paddles at the bottom of the receptacle. The control module 1010 in the base 1208 includes the logic to operate the impeller to dissolve the salt before operating the electrodes. Optionally, there may be sensors that determine the amount of undissolved salt in the receptacle 1202 that are sensed by the control module 1010. The control module 1010 then operates the electrodes at the appropriate time taking into account the amount of undissolved salt.

Further, this embodiment may operate for longer time periods, such as ten minutes, to ensure reaction completion. In embodiments, the receptacle can hold 64 ounces of solution, the current flow reverses every 2.5 minutes during operation, the operating amperage is 10 amps, the operating voltage ranges from 110 to 240 volts.

In embodiments of the medical receptacle design, various starting concentrations of reactants may be used. For example, 12 g of NaCl may be added to a ½ gallon of water to provide approximately 108.5 mM NaCl to start.

The Enlarged Receptacle Design, which may also be referred to as "Trio Maxx," shares much of the same components of the Portable Receptacle Design with several notable exceptions. For example, it employs an enlarged receptacle 1202 to be able to make a larger amount of ECA product solution. It may employ titanium electrodes that are coated with platinum, or any other electrode described herein, such as the iridium-coated electrodes, to resist corrosion and to have high electrical conductivity. This results in a device that has a cycle time of 3 to 5 minutes as opposed to the Portable Receptacle Design that has a cycle time of 5 minutes. In embodiments, the receptacle can hold 64 ounces of solution, the current flow is reversible at the halfway point during the 3 to 5 minute cycle, the operating amperage is 4 amps, the operating voltage ranges from 110 to 240 volts, and the wide mouth design facilitates brewing of 64 ounces of ECA product solution. Electrodes used in the Enlarged Receptacle Design may be platinum and/or titanium.

In embodiments of the enlarged receptacle design, various starting concentrations of reactants may be used. For example, 4 g of NaCl may be added to a ½ gallon of water to provide approximately 36 mM NaCl. In another example of a general purpose cleaner, 1.5 g of potassium carbonate may be added to a half gallon of water to provide approximately 5.7 mM potassium carbonate to start. Heavy duty cleaners and degreasers may utilize additional potassium carbonate (e.g. 4 g) such as to provide approximately 15.3 mM to start.

Figure 12F:
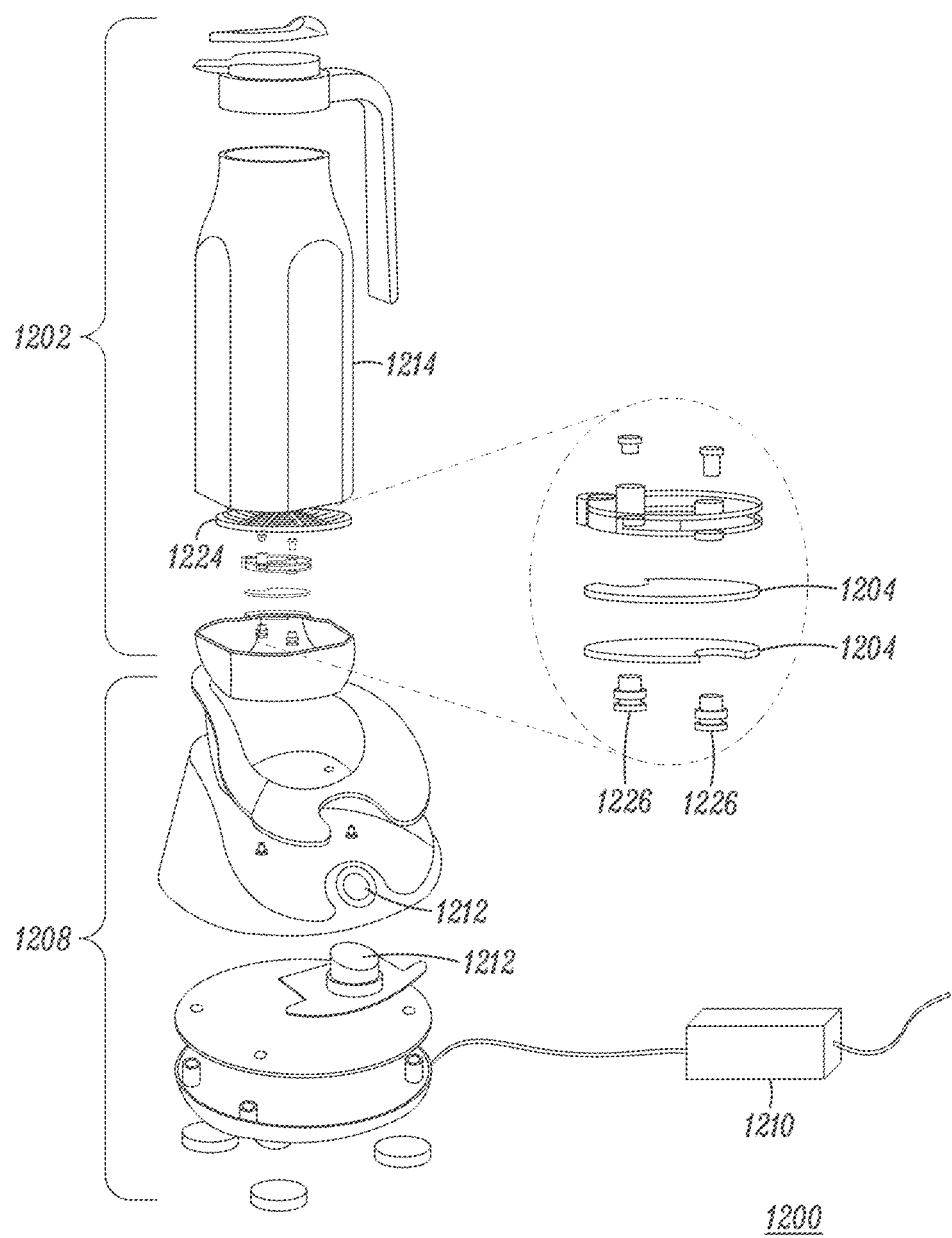
FIG. 12F depicts an exploded view of the receptacle apparatus of FIG. 12A.

FIG. 12F depicts an exploded view of the receptacle apparatus of FIG. 12A.

Here grating 1224 can be seen that prevents undissolved additives from building up around the electrodes 1204 and interfering with their performance.

Figure 12G:
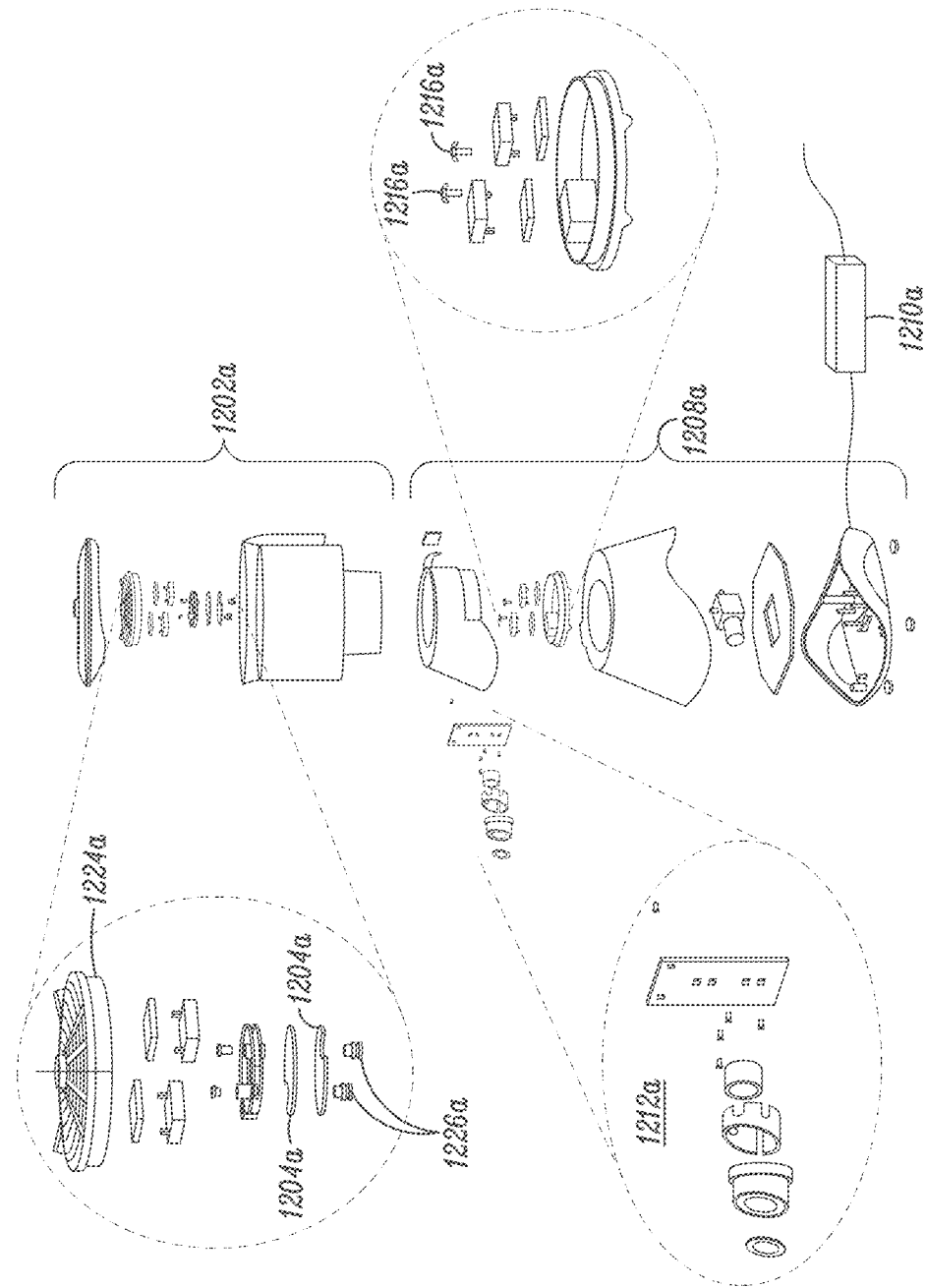
FIG. 12G depicts an exploded view of another receptacle embodiment.

FIG. 12G depicts an exploded view of another receptacle embodiment.

In this alternative embodiment, all parts having reference numbers that are the same as those described above (without the appended "a") serve a similar function and perform in a similar manner.

This includes a receptacle 1202a that fits into a base 1208a. Contact between electrodes 1216a and 1226a cause power to flow from the base 1208a to the electrodes 1204a in receptacle 1202a.

Power is provided to the system by a power supply 1210a.

It is shown here that a grating 1224a stops additives, such as salts from falling to the bottom of the container and affecting the operation of the electrodes 1204a.

A digital user interface 1212a interacts with the user to take commands and to provide status of the system.

Another embodiment of the system 1000 is the instant flow apparatus 1300 which is also referred to as a Continuous Flow Design or the "InstaFlow™" design. In this embodiment, water is received through an intake 1304 into an internal reservoir or electrode and reactant cell 1320. An optional intake sensor 1329 monitors the amount of fluid flow over a period of time and/or the rate of fluid flow being received. Also, an optional intake valve 1331 operates under the control of the controller 1312 and interactively regulates the amount of fluid received and/or the rate of fluid flow. An optional backflow preventer may prevent reactants from moving in a rearward direction into the water system. In addition, in embodiments, the system may contain various solenoids and valves to control the flow of fluids and air.

A salt is added to the water in the reservoir 1320. Alternatively, a salt-containing solution is taken into the apparatus 1300 via an intake 1304 into the reservoir 1320. The salt-containing solution comes in contact with the two or more electrodes 1310. A controller 1312, similar to the controller 1010 of FIG. 3, provides, or controls the provision of, electrical power to the electrodes 1310 to cause the electrochemical reactions to produce an ECA product solution.

The salt-containing solution may be held in the reservoir 1320 for a period of time or the reservoir 1320 may be continuously emptied of the product solution through the product outflow 1308 and refilled with fresh salt-containing solution. Optionally, an outflow sensor 1333 measures the rate of fluid flow and/or the accumulated fluid flow for a defined period of time. This information is provided to the controller 1312 that interactively operates an optional outflow valve 1335 that regulates the total amount of fluid released or the rate at which fluid is released.

The reservoir 1320 may optionally include an impeller 1322 for agitating the solution inside the reservoir 1320. The controller 1312 operates in a similar manner as the control module 1010 of FIG. 3 controlling various aspects and parameters of the system. In addition, the controller 1312 can adjust the rate in which the water is received as well as the rate in which the solution is removed from the internal reservoir 1320. Therefore, the rate at which the solution passes over the electrodes 1310 is controlled. The slower the solution passes over the electrodes 1310, the more time that it experiences becoming electrochemically activated. This causes an increase in the FAC (when producing the sanitizer solution, for example) and an increase in the concentration of $OH^-$ radicals (when producing the cleaning and degreasing solutions, for example) or an increase in the active species in other embodiments. A user may input the amount of reactant used or FAC desired and the controller 1312 may automatically program operation of the apparatus 1300.

The controller 1312 may include or be in communication with the sensors 1022 described herein to sense temperature, pH, FAC, current flow, solution level, and the other parameters noted herein and the like. It may also include additional sensors to monitor flow of water/solution in through the intake.

The controller 1312 may be operated by a user via manual means or via a digital user interface (UI) 1314. The apparatus 1300 may be powered by a power supply 1318, or other power means described herein.

Figure 13A:
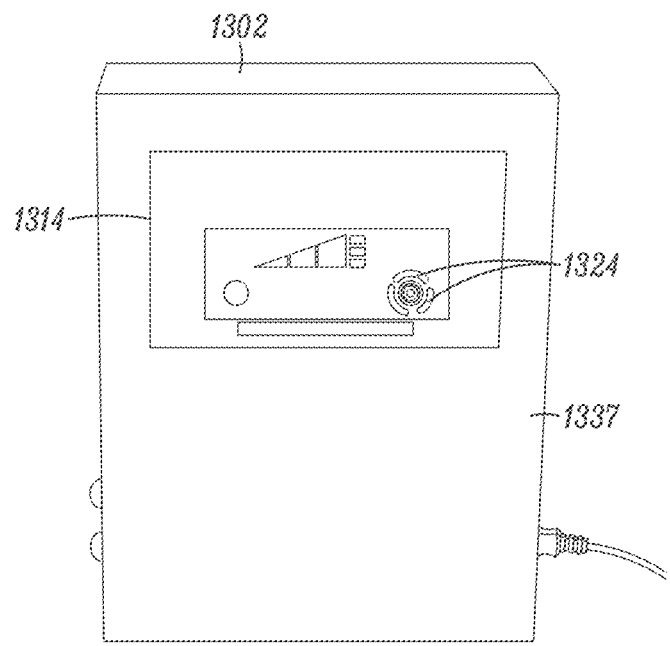
FIG. 13A depicts a front elevational view of the apparatus of FIG. 13.

FIG. 13A shows the Continuous Flow Design 1300 without the power supply 1318, the intake 1304 and product outflow 1308. The outer housing 1302 has a window for the digital UI 1314 which may have the features of the UI as described herein. It may include intuitive indications of the operation of the apparatus 1300. As indicated for the portable receptacle design above, there are operation indicators 1324 that are lights in a circular arrangement that sequentially light in a clockwise fashion when power is being provided in a first polarity to the solution, and in a counterclockwise fashion when power is being provided in a second polarity. The lights may also signify other activity, such as simultaneously flashing if an error has been sensed, or the system has run out of additives.

Figure 13B:
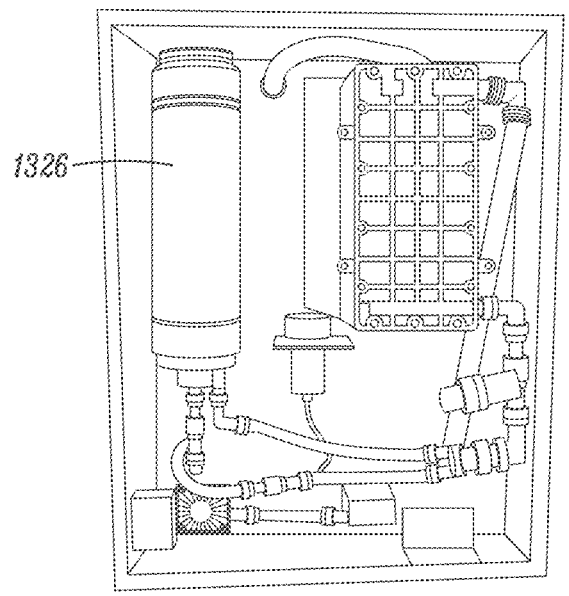
FIG. 13B depicts a rear elevational view of the apparatus of FIG. 13 with the cover removed.

FIG. 13B shows water handling elements of the system for the Continuous Flow Design 1300. Here an in-line filter 1326 filters out impurities from the tap water.

Figure 13C:
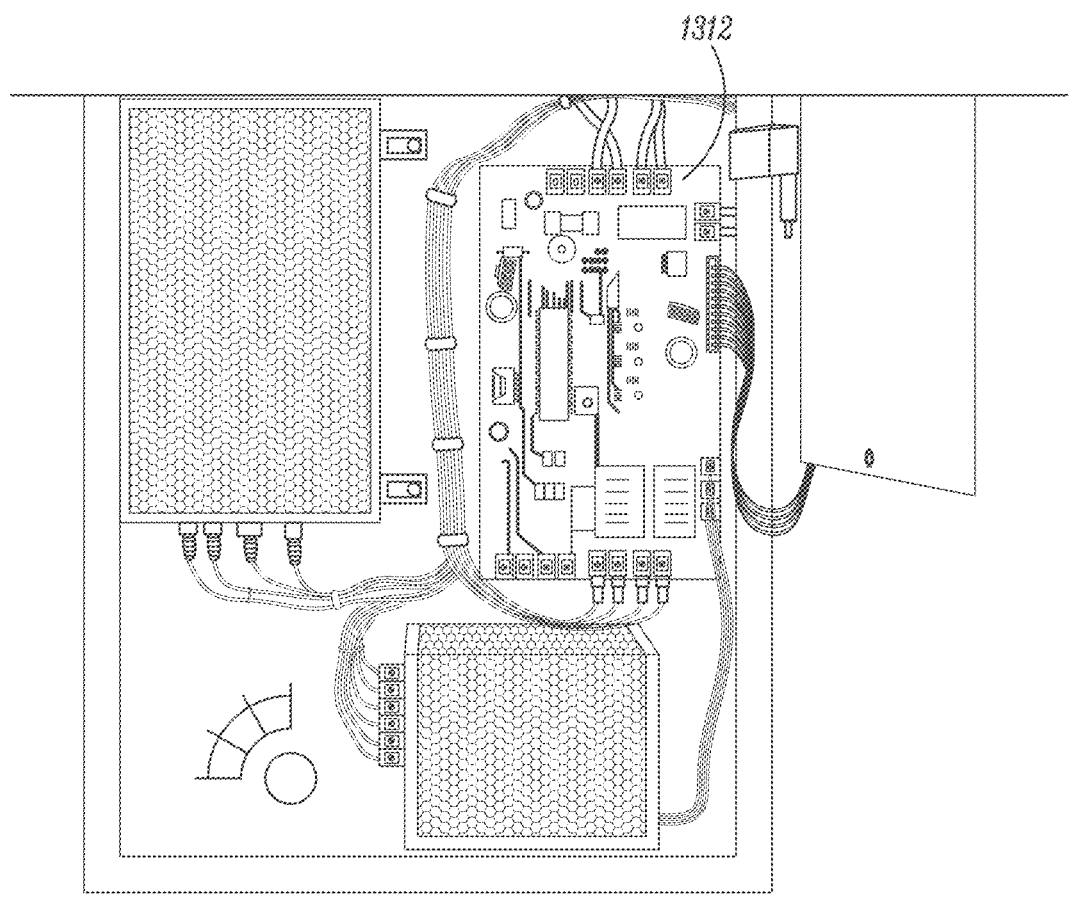
FIG. 13C depicts another rear elevational view of the apparatus of FIG. 13 with the cover removed.

FIG. 13C shows the system electronics for the Continuous Flow Design 1300. The controller 1312 is visible in this view.

The apparatus 1300 may have a reserve tank with automatic shut off.

In an embodiment, the Continuous Flow Design reverses current every 2 minutes when in operation and provides a continuous flow of ECA product solution of up to 2.5 gallons per minute. The Continuous Flow Design provides up to 17 Amps of current to the electrodes. The system can adjust the flow rate past the electrodes to adjust the amount of ECA activation of the solutions. The Continuous Flow Design can continuously operate at voltages ranging from 110-240 V and amperages of 17 amps or so. The Continuous Flow Design may be used as a table top unit or a wall-mounted unit. The Continuous Flow Design may utilize flat, rectangular electrodes.

In an embodiment, the continuous flow design may produce up to 450 gallons of ECA product solution per tank of reactant starting solution. In embodiments, at least 19 to 39 ounces of sodium chloride/citric acid mixture may be utilized in generating at least 70 gallons of the sanitizer, at least 13 ounces of potassium carbonate may be used to generate at least 65 gallons of the Heavy Duty Cleaner/Degreaser, and at least 6 Ounces of potassium carbonate may be used to generate at least 75 gallons of the Window and Glass Cleaner.

Figure 13D:
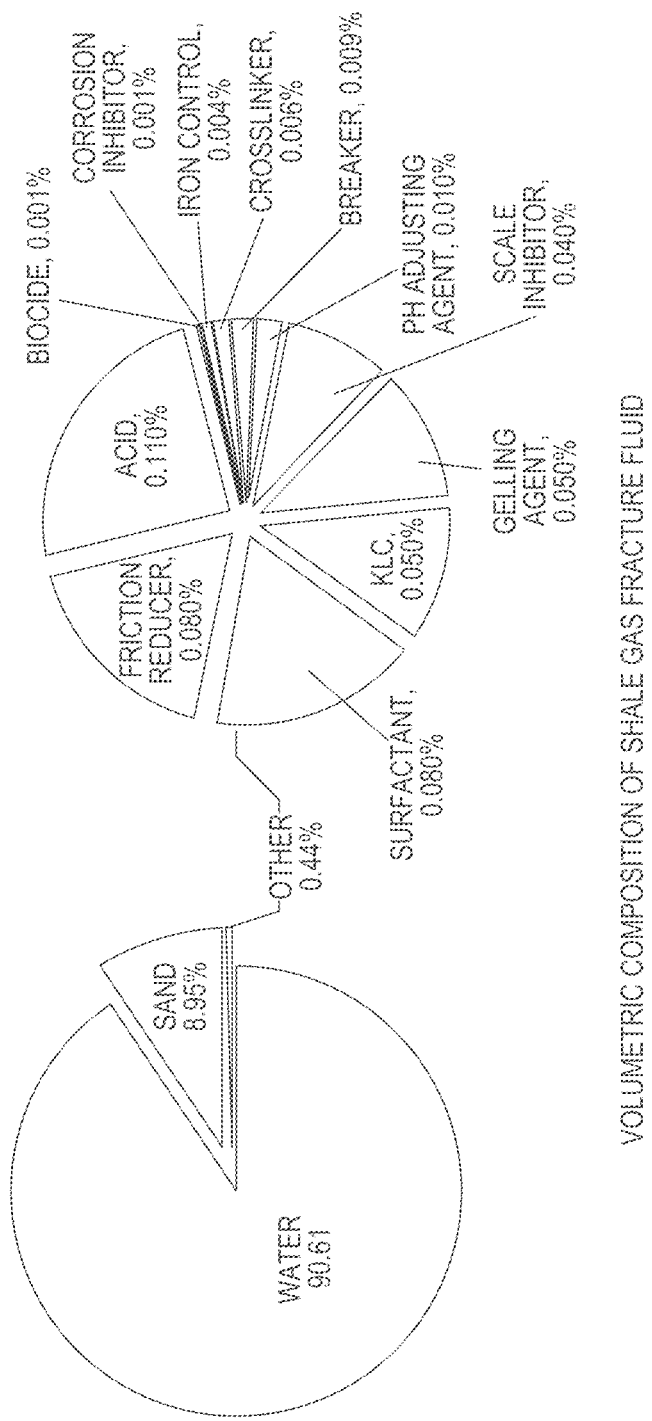
FIG. 13D depicts a pie chart illustrating an example of the composition of fracking fluids.

One of the uses for the products of the currently described system and method is in hydraulic fracturing, commonly called "fracking". Fracking typically requires large amounts of water with some sand and a small amount of other additives. FIG. 13D is an example of the volumetric composition of fracking fluids. Here it can be seen that the fracking fluid is approximately 90% water by volume. Approximately 9% is sand and the other additives make up approximately 0.5% by volume. The 0.5% of the other additives includes biocides such as Glutaraldehyde that eliminate bacteria in the water that produces corrosive by-products, as well as other chemicals, (from "Volumetric Composition of Shale Gas Fracture Fluid", http://www.shalegaswiki.com/index.php/Fracturing fluid).

The fracking fluid is forced down into a natural gas or oil well far below the surface into geological formations under high pressure by large fluid pumps. Up to 2 million gallons of water per day may be required to perform fracking for a single well. The biocide is about 0.001% by volume of this amount and may be needed in amounts of 2000 gallons of product per day.

Figure 13E:
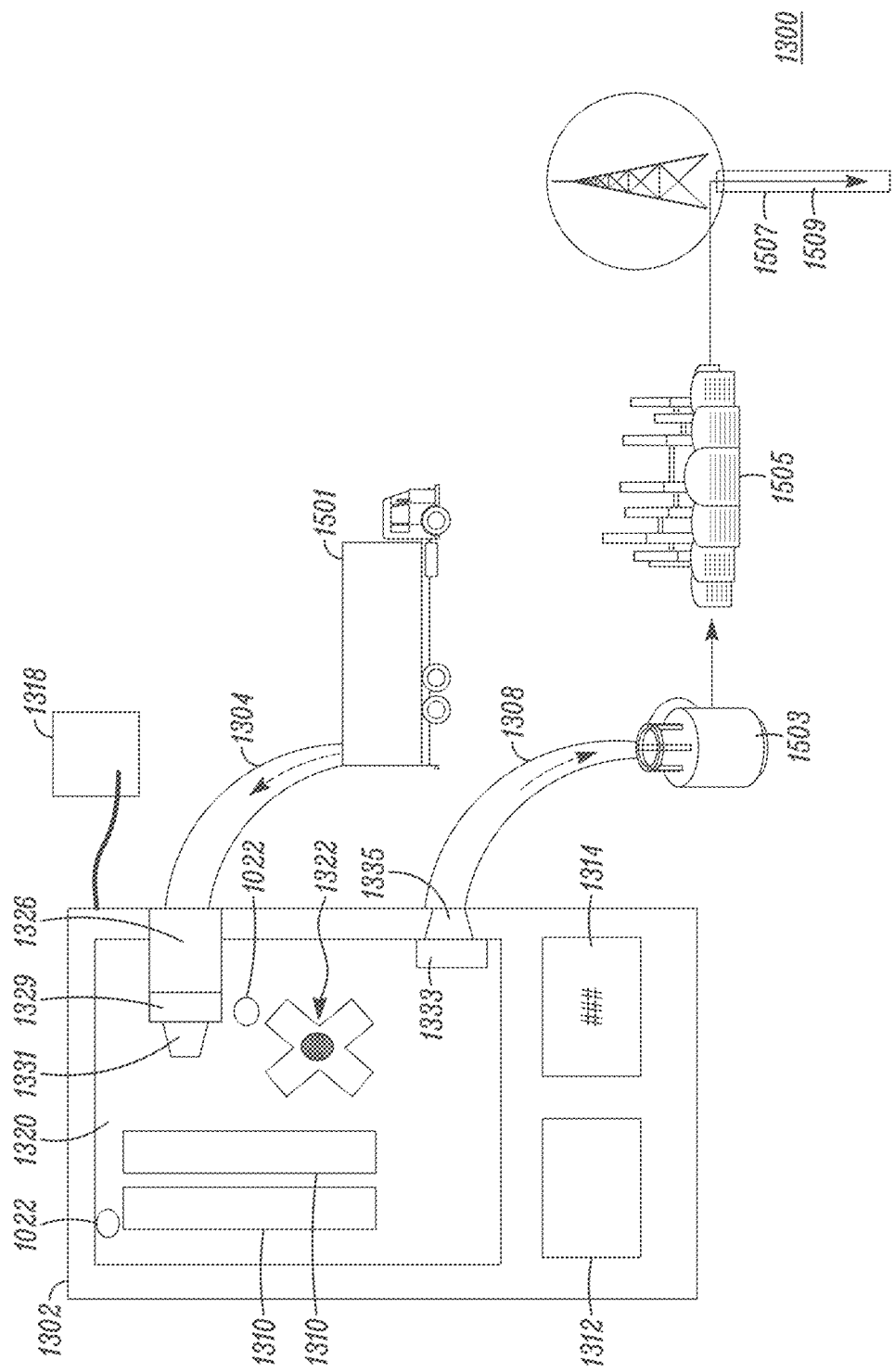
FIG. 13E depicts a continuous flow apparatus for use in the fracking industry.

Any of the embodiments described herein could be scaled to produce larger amounts of the ECA products. In particular, the continuous flow embodiment is well suited for use in connection with fracking. Referring now to FIG. 13E, an enlarged continuous flow system is shown. This functions in the same manner and employs the same functional structures as the continuous flow apparatus 1300 of FIG. 13, but is designed to be much larger to be able to provide the amount of ECA product required for fracking. In particular, the system may include a cell with an array of many electrodes as opposed to only a pair of electrodes.

Water to be used for fracking is shown here provided by a tanker truck 1501. In alternative embodiments, water may be provided by a water line leading to a water source such as a settling pool, pipeline, reservoir or other water source. The water is provided to the intake 1304. A salt, such as those described herein, is introduced into the water and mixed with the impeller 1322. The controller 1312 provides power to the electrodes 1310 in a manner to produce an ECA product that will be able to perform the function of a biocide or other functions useful for fracking applications. In other embodiments, potassium salts may be used to produce KOH used as a pH balancer. The ECA product exits the apparatus through the product outflow 1308 and into a holding tank 1503.

The ECA product is then provided to the fracking equipment that mixes it with water and sand, adds anticorrosion chemicals and other additives, gels the components into a fracking fluid and provides the components to a high pressure pump (typically part of fracking equipment 1505). The high pressure pump forces the fracking fluid through the casing of the well 1507, and down the well 1509 to perform its function underground.

The non-toxic ECA products may be used to replace at least some of the biocides currently used in fracking. The systems and methods described herein may also be used to develop other additives, such as hydrochloric acid that helps dissolve minerals and initiate cracks in rocks.

Figure 13F:
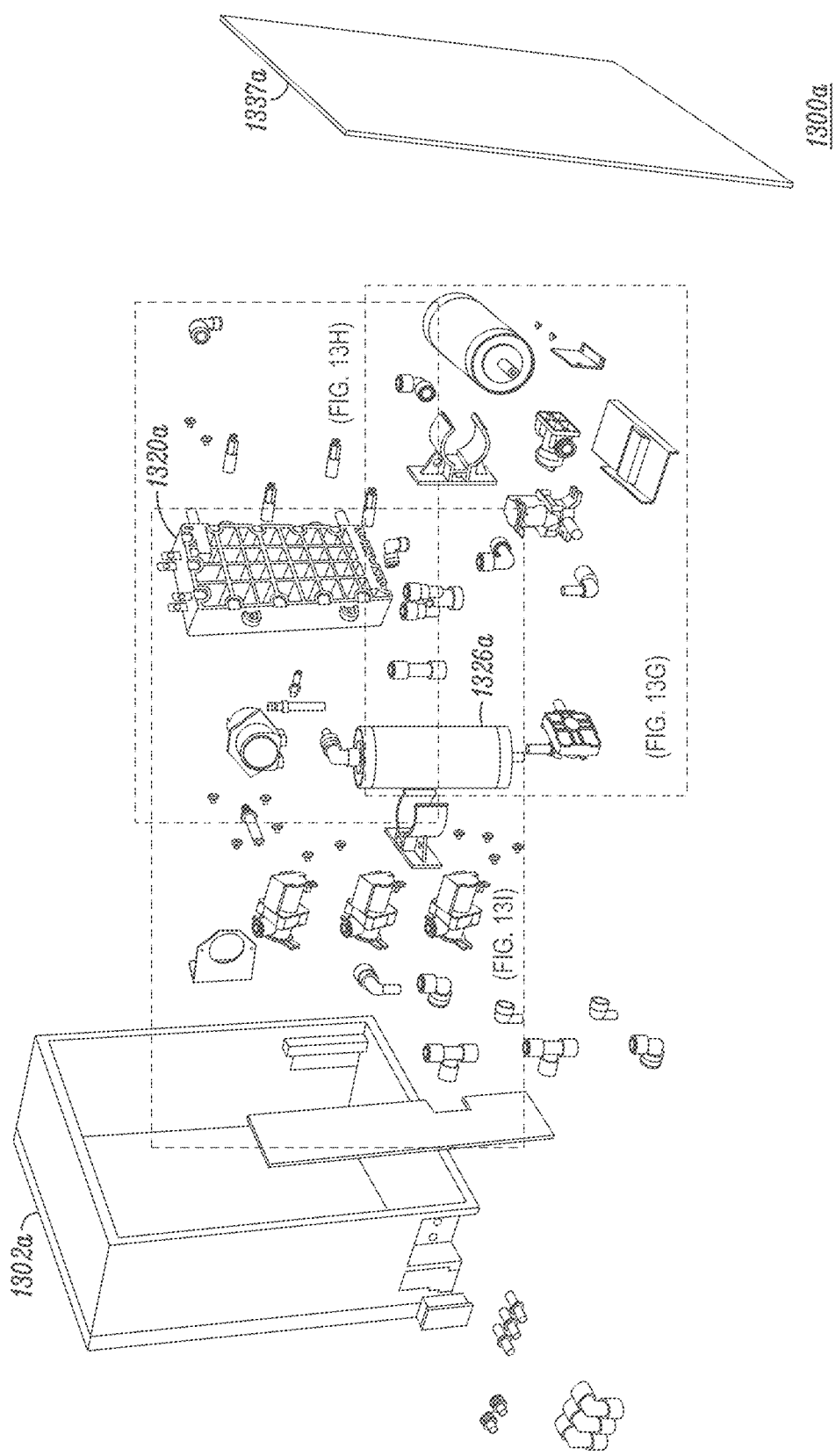
FIG. 13F depicts an exploded view of an alternative embodiment of an instant flow apparatus.

FIG. 13F depicts an exploded view of an alternative embodiment of an instant flow apparatus. Here are various pumps, valves, filters, sensors, etc. employed by the apparatus 1300a. In this view the reservoir 1320a is visible. Water filter 1326a is also visible. FIG. 13F is sectioned into three parts, each which is shown in subsequent FIGS., FIG. 13G, FIG. 13H and FIG. 13I.

Figure 13G:
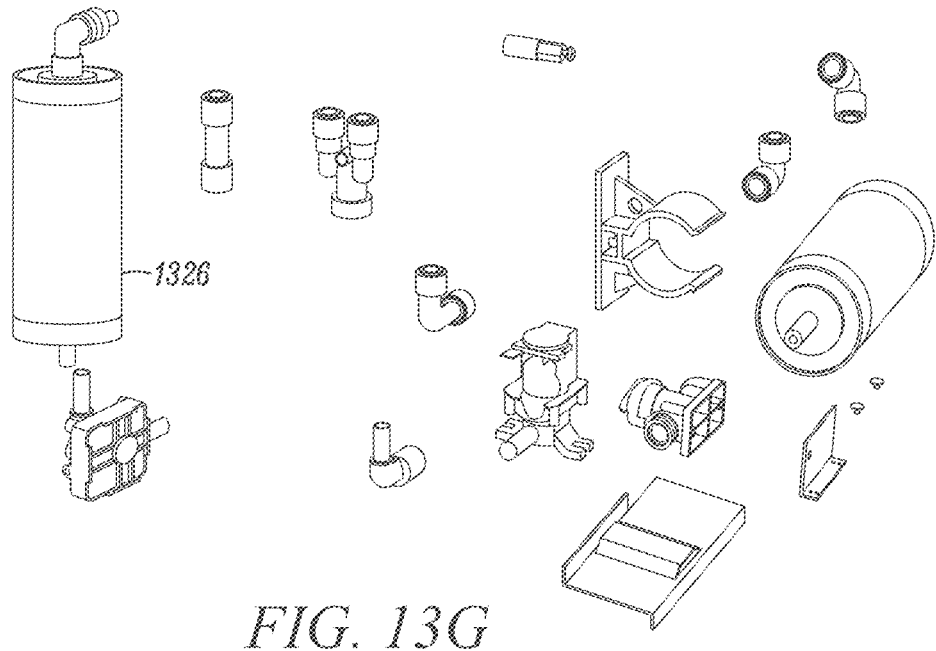
FIG. 13G is an enlarged view of elements of the instant flow apparatus of FIG. 13F.

FIG. 13G is an enlarged view of elements of the instant flow apparatus of FIG. 13F. The filter 1326 is shown here.

Figure 13H:
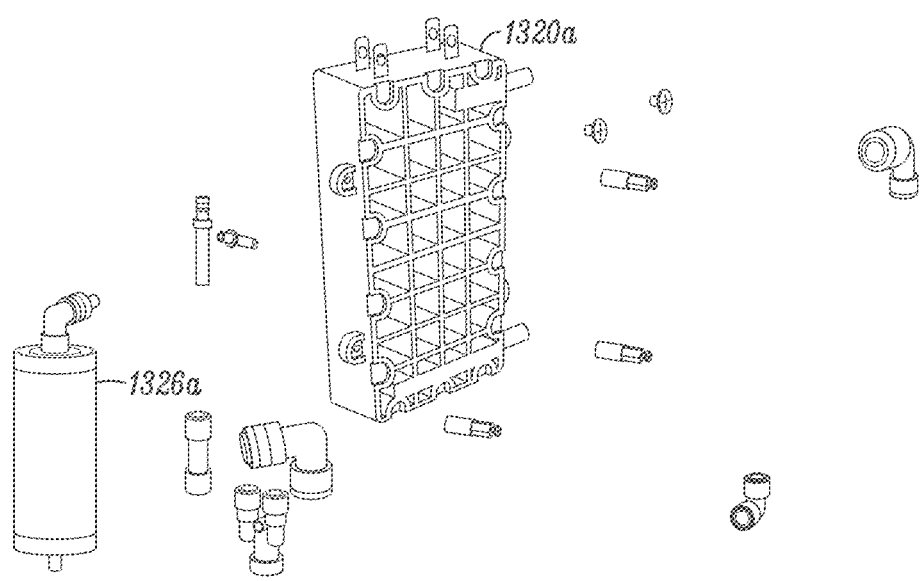
FIG. 13H is an enlarged view of elements of the instant flow apparatus of FIG. 13F.
Figure 13I:
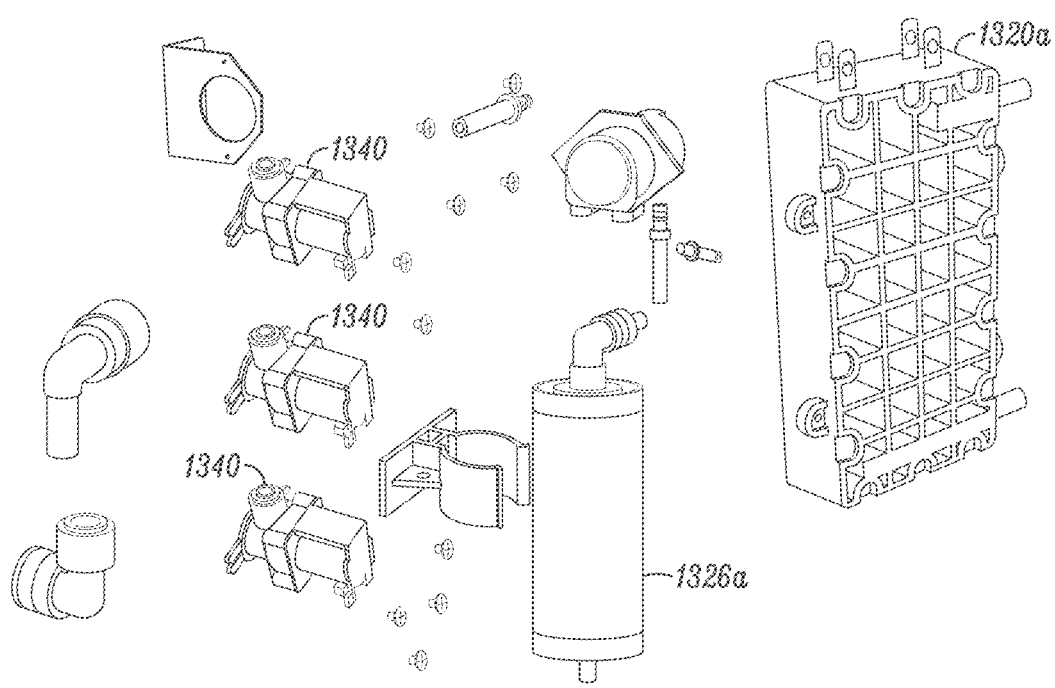
FIG. 13I is an enlarged view of elements of the instant flow apparatus of FIG. 13F.

FIG. 13H is an enlarged view of elements of the instant flow apparatus of FIG. 13F. In this view, both the reservoir 1320a and the filter 1326a are shown, FIG. 13I is an enlarged view of elements of the instant flow apparatus of FIG. 13F. Here, intake valves 1340 can be seen. In this embodiment, three intake valves 1340 are shown but it is understood that a plurality of intake valves 1340 may be used in the apparatus. For example, the plurality of intake valves 1340 may be useful for making a plurality of solutions readily. For example, a tank of starting solution containing reactants may be attached to the apparatus through the intake valve 1340. In the example of this apparatus, three tanks may be attached through the three intake valves 1340, each perhaps holding a different solution of starting reactants. For example, one tank could hold the sodium chloride/citric acid mixture, another holds potassium carbonate in sufficient quantity to produce a general purpose or glass cleaner, and yet another holds potassium carbonate in sufficient quantity to produce a degreaser/heavy duty cleaner. In any event, reactant solution taken up through the intake valve 1340 may be mixed with water either in the plumbing on the way to the reservoir 1320a or electrolysis chamber or within the reservoir 1320a or electrolysis chamber. In embodiments, the intake valve 1340 may take up water.

Figure 13J:
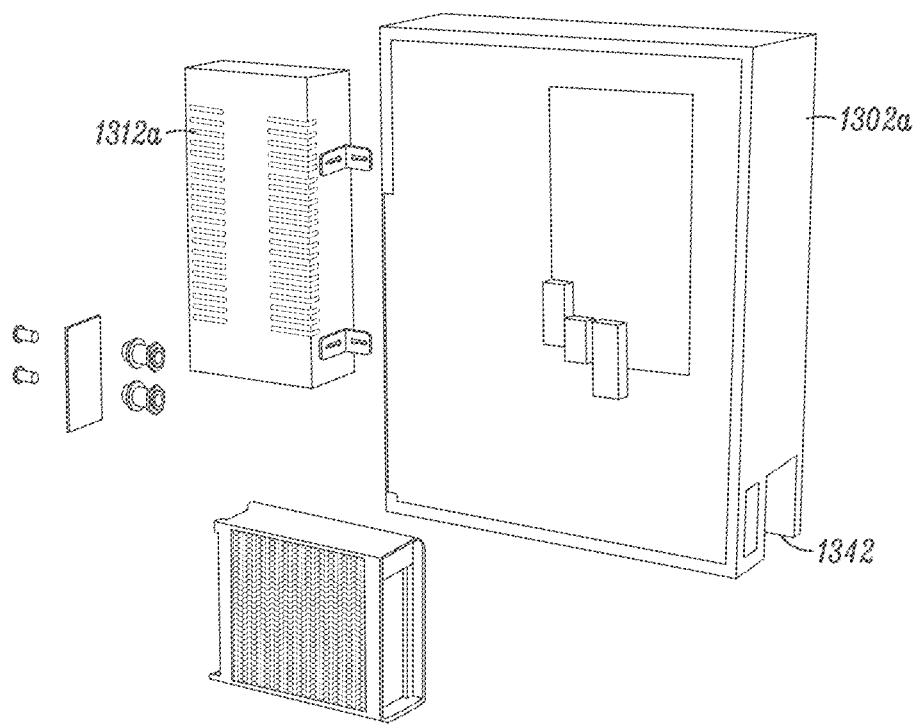
FIG. 13J depicts an exploded view of an alternative embodiment of an instant flow apparatus, showing the system electronics.

FIG. 13J depicts an exploded view of an alternative embodiment of an instant flow apparatus, showing the system electronics. Here, controller 1312a, which may be a 200 amp power controller, and housing 1302a are shown. On the housing 1302a, a three-line input 1342 for reactant intake is shown.

Figure 13K:
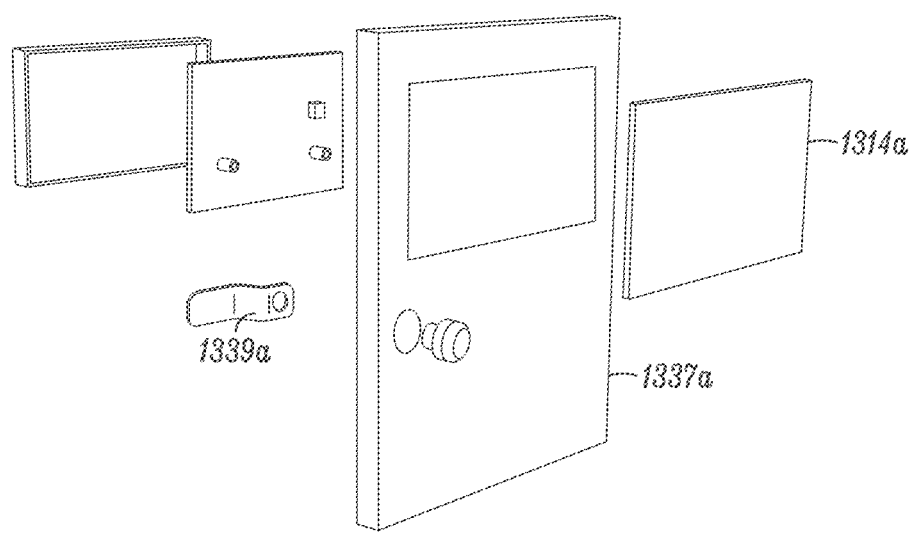
FIG. 13K depicts an exploded view of the front panel of an alternative embodiment of an instant flow apparatus.

FIG. 13K depicts an exploded view of the front panel assembly of an alternative embodiment of an instant flow apparatus.

Here it can be seen that a front panel 1337a has a latch 1339a. This latch 1339a attaches to the apparatus housing.

A digital User Interface (UI) 1314a allows the user to interact with the UI to receive input and provide status of the apparatus. The digital UI 1314a may comprise a liquid crystal display or any other display technology.

FIG. 14 is a table showing sample operating specifications for various particular embodiments of the present invention. It is to be understood that these are being provided as examples of specific embodiments keeping in mind that many variations and modifications of these specifications may also be used for additional embodiments of the current invention.

Since the ECA product solutions are non-toxic, they can be used in a variety of settings and applications. ECA product solutions may be used for cleaning, sanitizing and disinfecting food, kitchen utensils, cooking implements, hands, skin or any surfaces that may come in contact with microbes or dirt. Embodiments described herein may be deployed in various settings/environments or ECA product solutions may be used in various settings/environments/applications, such as: airplanes, trains, buses, taxis, cars, showers, bathrooms, schools, day cares, playgrounds, in situ microfiber cloth treatment, retail environments, hospitals, doctor's offices, medical facilities, wound care, veterinary facilities (e.g. as a halitosis treatment as well), pet stores, animal shelters, dental facilities (e.g. as an irrigant as well), nursing homes/elder care, pharmacies, emergency triage units, hotels, cruise ships, boats, shipboard wastewater treatment, spas, pools, gyms, saunas, salons, delis, butcher shops, grocery/produce section (e.g. in the produce sprayers), slaughterhouses, pelt cleaning, dairy farms (e.g. to clean milk production machinery), nut processing, mechanic shop, military/battlefield, mold remediation, laundry, warewashing, indoor air quality management, camping, third world/remote settlements, skin emollient, agricultural sprayer, plant mite killer, hydroponics irrigation, greenhouses, agricultural potassium source, wineries/vineyards, hydraulic fracking and the like.

ECA product solutions may also be used in food preparation, such as in restaurants and in fast food preparation, such as to clean fruits and vegetables or in warewashing. The ability to easily create ECA product solutions useful in food preparation may enable the use of local produce since such local produce, which may not be subject to regulatory inspection, can nevertheless meet regulatory standards. ECA product solutions may be used in food manufacturing/bottling/processing and in aseptic packaging. For example, in order to sanitize produce on site in a restaurant, the lettuce must be sprayed or soaked in a sanitizing solution. For large restaurants, keeping the quantity of sanitizing solution needed to soak produce, such as large heads of lettuce, that is discarded immediately to mitigate cross-contamination may require significant cost and storage. Utilizing the embodiments described herein to produce ECA product solutions suitable for sanitizing mitigates the need for maintaining an inventory of sanitizing solutions. Instead, sanitizing solutions can be made on demand in batches or in a continuous flow. Further, the only inventories required are the reactants and the generally compact embodiments.

In embodiments, the ECA system 1000 may be embodied as a produce sprayer or as a produce bath. For example, a produce sprayer may include a nozzle connected to a reservoir of embodiments of the ECA system 1000 or an outflow from embodiments of the ECA system 1000.

The ECA product solutions may be used for improving air quality by adding it to humidifiers or vaporizers for the home or in large building air handling facilities. It is also safe enough for use in a nursery, especially if someone in the house has contracted a cold. In embodiments, the ECA system 1000 may be integrated with the humidifier. For example, electrodes may be disposed within the reservoir of the humidifier to produce an ECA product solution such that it is the ECA product solution that gets released into the air by the humidifier, via any of the mechanisms by which humidifiers work. Use of the ECA product solutions in humidifiers and air handling facilities may be useful to mitigate the effects of asthma and allergies. Further, the humidifier need not be cleaned as frequently since the ECA product solution will clean, sanitize, and/or disinfect during use. It can be used in the exhaust for hot air furnaces. This will sanitize these hidden locations. Once in the air, ECA product solution can act as an airborne dust remover.

The ECA system, or its outputs, may be used in various form factors for hand and skin washing and sanitizing. In one embodiment of soapless hand washing, the ECA system may be deployed such that the outflow is directed to faucets for hand washing. In another embodiment, a wall-hanging dispenser may be filled with a stable output of the ECA system, such as the HOCl solution at a ppm below 200.

The ECA system may be integrated with various devices to produce ECA product solutions in situ, such as dishwasher/warewashing facilities, floor scrubber, washing machine/laundry facilities, produce sprayer, food washing bath, faucets (such as to provide soapless hand washing), shower heads, custodial sprayer, food sprayer/food bath, wall-mounted hand sanitizers, and the like. In certain embodiments, the ECA system may be retrofitted into existing devices. For example, a floor scrubber may have an onboard ECA system to produce ionized water or KOH on demand. In this example, the floor scrubber may have a reservoir. The electrodes used for ECA may be disposed within the reservoir. Control of the electrodes might be located among the controls for the floor scrubber itself such that a user of the scrubber can control production of the ECA product solution while operating, or not operating, the floor scrubber. The ECA product solution may be dispensed onto floors by an outflow from the reservoir. In another embodiment, the ECA system may be integrated with warewashing facilities. For example, as a warewashing facility takes up water for cleaning, the integrated ECA system may mix the water with reactants and flow the reactant solution over electrodes prior to dispensing it to the warewashing facility, which then dispenses the ECA product solution.

Wherever there are microbes and a need to sanitize/disinfect or if there is a need to clean, the ECA product solutions created by embodiments described herein may be used.

While only a few embodiments of the present invention have been shown and described, it will be obvious to those skilled in the art that many changes and modifications may be made thereunto without departing from the spirit and scope of the present invention as described in the following claims. All patent applications and patents, both foreign and domestic, and all other publications referenced herein are incorporated herein in their entireties to the full extent permitted by law.

The methods and systems described herein may transform physical and/or or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps associated therewith, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine-readable medium.

While the disclosure has been disclosed in connection with the preferred embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

The use of the terms "a" and "an" and "the" and similar referents in the context of describing the disclosure (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above described embodiment, method, and examples, but by all embodiments and methods within the scope and spirit of the disclosure.

All documents referenced herein are hereby incorporated by reference.

What is claimed is:

1. A floor scrubbing apparatus, comprising:
a reservoir for an aqueous salt solution disposed in the floor scrubbing apparatus;
an immersion device comprising a submersible housing with at least two iridium-coated electrodes spaced apart from each other within the submersible housing, wherein the immersion device is adapted to be immersed into the reservoir; and
a control module electrically coupled to the electrodes, wherein the control module controls application of electricity to cause a first electrode to be positively charged and a second electrode to be negatively charged,
wherein at least one of a distance and an angle or angles between the at least two iridium-coated electrodes is adjustable for the control module to control the application of electricity to the electrodes in a manner to perform electrochemical activation (ECA) of the aqueous salt solution in the reservoir to create an ECA product solution.

2. The floor scrubbing apparatus of claim 1, wherein the ECA product solution is selected from the group consisting of a sanitizing solution, a disinfecting solution, a cleaning solution, a degreasing solution, and an antimicrobial solution.

3. The floor scrubbing apparatus of claim 1, wherein the distance and the angle or angles between the at least two iridium-coated electrodes are automatically adjustable in response to a sensor that is sensing at least one product or by-product of the ECA of the aqueous salt solution.

4. The floor scrubbing apparatus of claim 3, wherein the sensor is in communication with the control module, and the sensor determines a concentration of free available chlorine in the solution within the reservoir.

5. The floor scrubbing apparatus of claim 1, wherein the aqueous salt solution is at least one of a sodium chloride solution, a mixture of sodium chloride and citric acid solution, a metal chloride salt solution and mixtures thereof, a metal halide salt solution, a metal carbonate solution, or a potassium carbonate solution.

6. The floor scrubbing apparatus of claim 5, wherein the metal halide salt is present in a trace amount in solution.

7. The floor scrubbing apparatus of claim 1, wherein the control module is programmed to reverse the polarity of the electrodes after a period of time.

8. The floor scrubbing apparatus of claim 1, further comprising at least one of an impeller and an on-board air pump disposed within the submersible housing for mixing at least one of the aqueous salt solution and the ECA product solution.

9. The floor scrubbing apparatus of claim 1, further comprising an impeller disposed on a surface of the submersible housing for mixing solution in the reservoir.

10. The floor scrubbing apparatus of claim 1, wherein the immersion device is powered by the kinetic energy generated from moving the floor scrubbing apparatus.

11. The floor scrubbing apparatus of claim 1, wherein the submersible housing is extendable to allow extension to the bottom of the reservoir.

12. The floor scrubbing apparatus of claim 1, wherein the distance and the angle or angles between the at least two electrodes are adjustable by a manual mechanism.

13. A floor scrubbing apparatus, comprising:
- a reservoir for an aqueous salt solution disposed in the floor scrubbing apparatus;
- at least two iridium-coated electrodes spaced apart from each other within the reservoir; and
- a control module electrically coupled to the electrodes, wherein the control module controls application of electricity to cause a first electrode to be positively charged and a second electrode to be negatively charged,
- wherein at least one of a distance and an angle or angles between the at least two iridium-coated electrodes is adjustable for the control module to control the application of electricity to the electrodes in a manner to perform electrochemical activation (ECA) of the aqueous salt solution in the reservoir to create an ECA product solution.

14. The floor scrubbing apparatus of claim 13, wherein the ECA product solution is selected from the group consisting of a sanitizing solution, a disinfecting solution, a cleaning solution, a degreasing solution, and an antimicrobial solution.

15. The floor scrubbing apparatus of claim 13, wherein the distance and the angle or angles between the at least two iridium-coated electrodes are automatically adjustable in response to a sensor that is sensing at least one product or by-product of the ECA of the aqueous salt solution.

16. The floor scrubbing apparatus of claim 15, wherein the sensor is in communication with the control module, and the sensor determines a concentration of free available chlorine in the solution within the reservoir.

17. The floor scrubbing apparatus of claim 13, wherein the aqueous salt solution is at least one of a sodium chloride solution, a mixture of sodium chloride and citric acid solution, a metal chloride salt solution and mixtures thereof, a metal halide salt solution, a metal carbonate solution, or a potassium carbonate solution.

18. The floor scrubbing apparatus of claim 17, wherein the metal halide salt is present in a trace amount in solution.

19. The floor scrubbing apparatus of claim 13, wherein the control module is programmed to reverse the polarity of the electrodes after a period of time.

20. The floor scrubbing apparatus of claim 13, further comprising an impeller within the reservoir for mixing at least one of the aqueous salt solution and the ECA product solution.

21. The floor scrubbing apparatus of claim 13, wherein the distance and the angle or angles between the at least two electrodes are adjustable by a manual mechanism.

* * * * *

UNITED STATES PATENT AND TRADEMARK OFFICE
CERTIFICATE OF CORRECTION

Page 1 of 1

PATENT NO. : 9,573,171 B2
APPLICATION NO. : 15/192472
DATED : February 21, 2017
INVENTOR(S) : John P. Shanahan et al.

It is certified that error appears in the above-identified patent and that said Letters Patent is hereby corrected as shown below:

In the Specification

In Column 1, Line 11, delete "application" and insert -- Application --, therefor.

In Column 1, Line 14, delete "application" and insert -- Application --, therefor.

In Column 36, Line 12, delete "shown," and insert -- shown. --, therefor.

Signed and Sealed this
Seventeenth Day of April, 2018

Andrei Iancu
*Director of the United States Patent and Trademark Office*